United States Patent [19]
Clarkson et al.

[11] Patent Number: 6,162,782
[45] Date of Patent: *Dec. 19, 2000

[54] DETERGENT COMPOSITIONS CONTAINING CELLULASE COMPOSITIONS DEFICIENT IN CBH I TYPE COMPONENTS

[75] Inventors: Kathleen A. Clarkson, San Francisco; Edward Larenas, San Carlos; Sharon Shoemaker, Fairfield; Geoffrey L. Weiss, San Francisco, all of Calif.

[73] Assignee: Genencor International, Inc., Palo Alto, Calif.

[*] Notice: This patent is subject to a terminal disclaimer.

[21] Appl. No.: 08/463,518

[22] Filed: Jun. 5, 1995

Related U.S. Application Data

[63] Continuation of application No. 08/152,099, Nov. 15, 1993, which is a continuation of application No. 07/713,738, Jun. 11, 1991, abandoned, which is a continuation-in-part of application No. 07/593,919, Oct. 5, 1990, abandoned.

[51] Int. Cl.$^7$ .................................................... C11D 3/386
[52] U.S. Cl. ......................... 510/320; 510/295; 510/307; 510/392; 510/393; 510/515; 510/530; 436/269; 8/137
[58] Field of Search .................. 256/174.12, DIG. 12; 435/209, 264; 510/295, 305, 320, 392, 393, 515, 516; 8/137

[56] References Cited

U.S. PATENT DOCUMENTS

| | | | |
|---|---|---|---|
| 3,415,804 | 12/1968 | Polson | 260/112 |
| 4,016,039 | 4/1977 | Schriber | 195/66 R |
| 4,144,130 | 3/1979 | Kula et al. | 195/66 R |
| 4,275,163 | 6/1981 | Gallo | 435/209 |
| 4,343,735 | 8/1982 | Menge et al. | 260/112 R |
| 4,385,443 | 5/1983 | Weissman et al. | 435/6 |
| 4,394,443 | 7/1983 | Weissman et al. | 435/6 |
| 4,435,307 | 3/1984 | Barbesgaard et al. | 252/174.12 |
| 4,439,358 | 3/1984 | Coan et al. | 260/112 B |
| 4,443,355 | 4/1984 | Murata et al. | 252/174.12 |
| 4,470,969 | 9/1984 | Pancham et al. | 424/101 |

(List continued on next page.)

FOREIGN PATENT DOCUMENTS

| | | |
|---|---|---|
| 0 120 528 | 10/1984 | European Pat. Off. . |
| 0 137 280 | 4/1985 | European Pat. Off. . |
| 0 173 397 | 3/1986 | European Pat. Off. . |
| 0 220 016 | 4/1987 | European Pat. Off. . |
| 0 244 234 | 11/1987 | European Pat. Off. . |
| 0 271 004 | 6/1988 | European Pat. Off. . |
| 0 538 977 | 3/1992 | European Pat. Off. . |
| 2 108 069 | 9/1971 | France . |
| 58-36217 | 3/1983 | Japan . |

(List continued on next page.)

OTHER PUBLICATIONS

Aho, "Structural and functional analysis of *Trichoderma reesei* endoglucanase I expressed in yeast *Saccharomyces cerevisiae*" *FEBS Letters* 291:45–49 (1991).

American Type Culture Collection *Catalogue of Filamentous Fungi* p. 412 (1991).

Anderson et al., "α–Amylase production in aqueous two–phase systems with Bacillus subtilis" *Enzymes and Microb. Technol.* 7:333–338 (1985).

Ballance et al. "Transformation of *Aspergillus nidulans* by the orotidine–5'–phosphate decarboxylase gene of *Neurospora crassa*" *Biochem. Biophys. Res. Comm.* 112(1):284–289 (1983).

(List continued on next page.)

Primary Examiner—Kery A. Fries
Attorney, Agent, or Firm—Burns, Doane, Swecker & Mathis, L.L.P.

[57] ABSTRACT

Disclosed are cellulase compositions containing one or more endoglucanase components and less than about 5 weight percent of CBH I type components. When incorporated into detergent compositions and used in acidic, neutral, or alkaline washing media, such cellulase compositions impart color retention/restoration properties as well as improved softening properties to cotton-containing fabrics. Additionally, such compositions impart reduced strength loss to cotton-containing fabrics as compared to cellulase compositions containing greater amounts of CBH I type components.

18 Claims, 10 Drawing Sheets

U.S. PATENT DOCUMENTS

| | | | |
|---|---|---|---|
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,508,825 | 4/1985 | Kim et al. | 435/210 |
| 4,591,563 | 5/1986 | Paul et al. | 435/193 |
| 4,648,979 | 3/1987 | Parslow et al. | 252/8.8 |
| 4,661,289 | 4/1987 | Parslow et al. | 252/547 |
| 4,683,294 | 7/1987 | Van Wijendaele et al. | 530/371 |
| 4,684,723 | 8/1987 | Dove et al. | 530/351 |
| 4,697,003 | 9/1987 | Coan | 530/380 |
| 4,725,544 | 2/1988 | Tan et al. | 435/200 |
| 4,728,613 | 3/1988 | Brewer et al. | 435/222 |
| 4,738,682 | 4/1988 | Boegh et al. | 8/401 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174.12 |
| 4,832,864 | 5/1989 | Olson | 252/174.12 |
| 4,885,249 | 12/1989 | Buxton | 435/172.3 |
| 4,894,338 | 1/1990 | Knowles et al. | 435/172.3 |
| 4,912,056 | 3/1990 | Olson | 435/263 |
| 4,945,053 | 7/1990 | Ito et al. | 435/263 |
| 4,952,505 | 8/1990 | Cho | 435/209 |
| 4,978,470 | 12/1990 | Suzuki et al. | 252/174.12 |
| 5,006,126 | 4/1991 | Olson et al. | 8/401 |
| 5,045,464 | 9/1991 | Ito et al. | 435/209 |
| 5,073,391 | 12/1991 | DeMars et al. | 426/231 |
| 5,120,463 | 6/1992 | Bjork et al. | 252/174.12 |
| 5,122,159 | 6/1992 | Olson et al. | 8/401 |
| 5,124,066 | 6/1992 | Russell | 252/174.12 |
| 5,139,943 | 8/1992 | Heinsohn et al. | 435/226 |
| 5,151,355 | 9/1992 | Heinsohn et al. | 435/226 |
| 5,232,851 | 8/1993 | Cox et al. | 435/263 |
| 5,246,853 | 9/1993 | Clarkson et al. | 435/263 |
| 5,290,474 | 3/1994 | Clarkson et al. | 252/174.12 |
| 5,298,408 | 3/1994 | Nevalainen et al. | 435/209 |
| 5,318,905 | 6/1994 | Saito et al. | 435/209 |
| 5,328,841 | 7/1994 | Lorch et al. | 435/209 |
| 5,352,243 | 10/1994 | Ashizawa et al. | 8/401 |
| 5,419,778 | 5/1995 | Clarkson et al. | 8/116.1 |

FOREIGN PATENT DOCUMENTS

| | | |
|---|---|---|
| 58-54082 | 3/1983 | Japan . |
| 62-062898 | 3/1987 | Japan . |
| 64-40681 | 2/1989 | Japan . |
| 51-15293 | 5/1993 | Japan . |
| 21 48 278 | 3/1972 | United Kingdom . |
| 1 368 599 | 10/1974 | United Kingdom . |
| 2 094 826 | 9/1982 | United Kingdom . |
| 2 095 275 | 9/1982 | United Kingdom . |
| 85/04672 | 10/1985 | WIPO . |
| 8909259 | 10/1989 | WIPO . |
| 90/02790 | 3/1990 | WIPO . |
| 90/15866 | 12/1990 | WIPO . |
| 9105841 | 5/1991 | WIPO . |
| 91/10732 | 7/1991 | WIPO . |
| 91/13136 | 9/1991 | WIPO . |
| 91/17243 | 11/1991 | WIPO . |
| 91/18978 | 12/1991 | WIPO . |
| 92/03541 | 3/1992 | WIPO . |
| 92/06165 | 4/1992 | WIPO . |
| 92/06183 | 4/1992 | WIPO . |
| 92/06184 | 4/1992 | WIPO . |
| 92/06210 | 4/1992 | WIPO . |
| 92/06221 | 4/1992 | WIPO . |
| 92/07134 | 4/1992 | WIPO . |
| 9206165 | 4/1992 | WIPO . |
| 92/17572 | 10/1992 | WIPO . |
| 92/17574 | 10/1992 | WIPO . |
| 93/15186 | 8/1993 | WIPO . |
| 93/20278 | 10/1993 | WIPO . |
| 9322414 | 11/1993 | WIPO . |
| 94/07983 | 4/1994 | WIPO . |
| 94/07998 | 4/1994 | WIPO . |
| 94/23113 | 10/1994 | WIPO . |

OTHER PUBLICATIONS

Bazin, et al., "Cellulasebehandlung von Cellulosewaren mit Hilfe von Enzymen" *Texile Praxis Internation* 47(10) (Oct. 1992).

Beach et al., "High–frequency transformation of the fission yeast *Schizocaccharomyces pombe*" *Nature* 290:140–142 (1981).

Bealin–Kelly et al, "Studies on the thermostability of the alpha–amylase of bacillus–caldovelox" *Appl. Microbiol. and Biotech* 36(3):332–336 (Dec. 1991).

Beggs, J.D. "Transformation of Yeast by Replicating Hydrid Plasmid" *Nature* 275:104–109 (1978).

Berg et al., "Enzyme–Gold Affinity Labelling of Cellulose" *Journal of Electron Microsc. Tech.* 8(4):371–379 (Apr. 1988) Abstract.

Berges and Barreau "Isolation of uridine auxotrophs from *Trichoderma reesei* and efficient transformation with the cloned ura3 and ura5 genes" *Current Genetics* 19:359–365 (1991).

Bhat et al., "The Endo–(1–4)–β–D–Glucanase System of *Penicillium pinophilum* Cellulase: Isolation, Purification, and Characterization of Five Major Endoglucanase Components" *Carbohydrate Research* 190:279–297 (1989).

Bhikhabhai et al., "The cellulotyic enzymes of *trichoderma reesei* as a system of homologous proteins" *FEBS Letters* 169(2):301–309 (Feb. 1984).

Brown and Gritzali, "Microbial Enzymes and Lignocellulose Utilization" *Genetic Control of Environmental Pollutants*, Omenn Editor, Plenum Publisher, pp. 239–265 (1984).

Brosnan, et al., "Investigation of the mechanism of irreversible thermoinactivation of bacillus–stearothermophilus alpha–amylase" *Eur. J. of Biochem.* 203(1–2)225–231 (Jan. 1992).

Boucher, et al., "Complete nucleotide sequence of the xylanase gene from the yeast *Cryptococcus albidus*" *Nucleic Acid Research* 16(20):9874 (1988).

Buschle–Diller, et al., "Enzymatic Hudrolysis of Cotton, Linen, Ramie, and Viscose Rayon Fabrics" *Textile Research Journal* 64(5):270–279 (May 1994).

Cannon, P.F., "International Commission of the Taxonomy of Fungi (ICTF): name changes in fungi of microbiological, industrial and medical importance", *Microbiological Sciences* 3:285–287 (1986).

Carter et al., "Chromosomal and genetic analysis of the electrophoretic karyotype of *Trichderma reesei*:mapping of the cellulase and xylanase genes" *Molec. Microb.* 6(15):2167–2174 (1992).

Case et al., "Efficient transformation of *Neurospora crassa* by utilizing hybrid plasmid DNA" *Proc. Natl. Acad. Sci. USA* 76(10):5259–5263 (1979).

Case, "Genetical and Molecular Analyses of QA–2 Transformants in *Neurospora crassa*" *Genetics* 113:569–587 (1986).

Chauthaiwale, et al., Molecular cloning of xylanase genes from Chainia in E.coli gene cloning: plasmid pUC8, plasmid pTZ18R–based vector constuction and expression in E. coli *Abstr. Gen. Meet. Am. Soc. Microbiol.* 91 Meet. 189 (1991) [Abstract].

Chen et al., "Nucleotide Sequence and Deduced Primary Structure of Cellobiohydrolase II from *Trichoderma reesei*" *Biotechnology* 5:274–278 (1987).

Clarke, D., "Enzyme treatment for removing pills from garment dyed goods" *International Dyer* 178(7):20–21 (1993).

Corrick et al., "The Nucleotide Sequence of the amdS Gene of *Aspergillus nidulans* and the Molecular Characterization of 5' Mutations" *Gene* 53:63–71 (1987).

Coughlan et al., "Comparative Biochemistry of Fungal and Bacterial Cellulolytic Enzyme Systems" *Biochemistry and Genetics of Cellulose Degradation* Aubert et al Eds., pp. 11–30 (1988).

Dhawale et al., "Transformation of *Neurospora crassa* with circular and linear DNA and analysis of the fate of the transforming DNA" *Current Genetics* 10:205–212 (1985).

Ellouz et al., "Analytical separation of Trichoderma reesie cellulases by ion–exchange fast proetein liquid chromatography" *J. of Chromatography* 396:307–317 (1987) [Abstract].

Fincham, "Transformation of Fungi" *Microbiol. Rev.* 53:148–170 (1989).

Fukusaki, et al., The complete nuclotide sequence of the xylanase gene (xynA) of *Bacillus pumilus FEBS 1512* 171(2):197–201 (Jul. 1984).

Gilkes et al., "Domains in Microbial β–1,4–Glycanases:Sequence Conservation, Function and Enzyme Families" *Microbiological Reviews* 55:303–315 (1991).

Gong, et al., "Biosynthesis, Pruification, and Mode of Action of Cellulases of *Trichoderma reesei*" *Hydrolysis of Cellulose* pp. 261–287 (1979).

Gruber et al., "Cloning of the *Trichoderma reesei* pyrG gene and its use as a homologous marker for a high–frequency transformation system" *Current Genetics* 18:447–451 (1990).

Gruber et al., "The development of a heterologous transformation system for the cellulolytic fungus *Trichoderma reesei* based on pyrG–negative mutant strain" *Current Genetics* 18:71–76 (1990).

Hakansson et al., "Purification and characterization of a Low Molecular Weight 1,4–β–Glucan Glucanohydrolase from the Cellulolytic Fungus *Trichoderma viride* OM 9414" *Biochimica et Biophysica Acta* 524:385–392 (1978).

Hakansson, Dissertation, Faculty of Science, Uppsal University, pp. 6–23 (1981).

Harkki et al., "Genetic engineering of Trichoderma to produce strains with novel cellulase profiles" *Enzyme Microb. Technol.* 13:227–233 (1991).

Hayashida et al., "Production and Purification of Thermostable Cellulases from *Humicola insolens*" *Agric. Biol. Chem.* 44(8):1721–1728 (1980).

Hayashida et al., "The Role of Carbohydrate Moiety on Thermostability of Cellulases from *Humicola insolens* YG–8" *Agri. Biol. Chem.* 44(3):481–487 (1980).

Hayashida, et al., "Cellulases of *Humicola insolens* and *Humicola grisea*" Methods in Enzymology 160:323–332 (1988).

Hinnen, A. et al., "Transformation of yeast" *Proc. Natl. Acad. Sci. USA* 75(4):1929–1933 (1978).

Innovations, "Back Staining, A Problem? Not Anymore!" 2 pages (1991).

*International Textile Bulletin, Dyeing/Printing/Finishing*, "Softening and Polishing of Cotton Fabrics by Cellulase Treatment" (2nd Quarter, 1990) pp. 5–8 (1990).

Irie et al., *Hakkikogaku Kaishi* 86(6):457–464 (1990) [Abstract].

JTN "Weight Loss Treatment to Soften the Touch of Cotton Fabric" p. 64 (Dec. 1988).

Kenkyushitsu et al., "The Improvement of Cellulose Fibers by Means of Cellulase" pp. 54–61.

Kim et al., Transformation of *Neurospora crassa* with trp–1 gene and the effect of host strain upon the fate of the transforming DNA *Current Genetics* 13:65–70 (1988).

Kimmel, A., Selection of Clones from Libraries:Overview *Methods in Enzymology* 152:393–399 (1987).

Knowles et al., "The use of gene technology to investigate fungal cellulolytic enzymes *Trichoderma reesei* cellulase complex gene cloning and expression in *Saccharomyces cerevisiae*" *FEMS Symp.* 43:153–169 (1988) [Abstract].

Knowles et al., "The use of gene technology in the development of novel cellolytic organisms—*Trichoderma reesei* cellulase and celluloiohydrolase gene cloning and expression; a review" *Recent Adv. Biotechnol. Appl. Biol.* pp. 139–142 (1988) [Abstract].

Kochavi et al., "Optimizing Processing conditions in Enzymatic Stonewashing" *Amer. Dystruff Reporter*, pp. 24, 26 and 28 (Sep. 1990).

Kubicek–Pranz et al., "Characterization of Commercial *Trichoderma–reesei* Cellulase Preparations by Denaturing Electrophoresis SDS–Page and Immunostaining Using Monoclonal Antibodies" *Biotechnol. Appl. Biochem.* 14(3):317–323 (1991) [Abstract].

Kubicek–Pranz et al., "Transformation of *Trichoderma reesei* with cellobiohydrolase II gene as a means for obtaining strains with increased cellulase production and specific activity" *Journal of Biotechnology* 20:83–94 (1991).

Kula et al., "Purification of Enzymes by Liquid–Liquid Extraction" pp. 73–118.

Kyviacou et al., *Enzyme Microb. Technology* 9(1):25–32 (1987).

Lappalainen et al., *Biotechnol. Appl. Biochem* 8(5):437–45 [abstract].

Lopes et al., "High–copy–number integration into the ribosomal DNA of Saccaromyces cerevisiae: a new vector for high–level expression–plasmid pMIRY2 construction with ribosome DNA; phosphoglycerate–kinase, superoxide–dismutase and thaumatin gene cloning" *Gene* 79(2):199–206 (1989) [Abstract].

Luderer et al., "A Re–appraisal of Multiplicity of Endoglucanase I from *Trichoderma reesei* Using Monoclonal Antibodies and Plasma Desorption Mass Spectrometry" *Biochim. Biophys. Acta* 1076:427–434 (1991) [Abstract].

Messner et al., "Cellobiohydrolase II is the main conidial–bound cellulase in *Trichoderma reesei* and other Trichoderma strains" *Archives of Microbiology* 155(6):601–606 (1991).

Miller et al., "Direct and Indirect Gene Replacements in *Aspergillus nidulans*" *Mol. and Cell. Biol.* 5(7):1714–1721 (1985).

Murphy–Holland et al., "Secretion activity and stability of deglycosulated cellulase of *Trichoderma reesei* gene cloning" *Abstr. Annu. Meet. Am. Soc. Microbiol.* 85th Meeting, vol. 193 (1985) [Abstract].

Nevalainen, H., "Genetic improvement of enzyme production in industrially important fungal strains" *Technical Research Center of Finland, Publications* 26:39–41 (1985).

Novo Enzymes, Celluclast, 4 pages.

Ohishi et al., "Reformation of Cotton Fabric by Cellulase" pp. 1–12.

Paietta, J.V. et al., "Gene disruption by transformation in *Neurospora crass*" *Mol. Cell. Biol.* 5(7):1554–1559 (1985).

Pentilla et al., "Construction of brewer's yeast secreting fungal endo–beta glucanase–recombinant cellulase preparation by protein secretion by Saccharomyces cerevisiae transformation" *Current Genetics* 12(6):413–420 (1987) [Abstract].

Penttila et al., "Homology between cellulase genes of *Trichoderma reesei*:complete nucleotide sequence of the endoglucanase I gene" *Gene* 45:253–263 (1986).

Penttilla et al., "Expression of Two *Trichoderma reesei* Endoglucanases the Yeast *Saccharomyces cerevisiae*" *Yeast* 3:175–185 (1987).

Reinikainen et al., "How do *Trichoderma reesei* cellobiohydrolase bind to and degrad cellulose?—cellobiohydrolase and cellulase characterization", *Abstr. Pap. Am. Chem. Soc.* 202 Meet. Pt. 1, (1991) [Abstract].

Royer et al., "Xylanase of Trichoderma longibrachiatum production and characterization" *Abstr. Annu. Meet. Am. Soc. Microlbiol.*, 85th Meet. 236 (1985) [abstract].

Saddler et al., Purification and application of hemicellulose modifying enzymes—*Trichoderma reesei* large–scale endo–1,4–beta–D–xylanase production; xylan degradation *Am. Chem. Soc.*, 195 Meeting, Cell 198 (1988) [abstract].

Saloheimo et al., "EGIII a new endoglucanase from *Trichoderma reesei*: the characterization of both gene and enzyme" *Gene* 63:11–21 (1988).

Sambrook et al., *Molecular Cloning A Laboratory Manual* 2nd Ed. Cold Spring Harbor Laboratory Press, pp. 1.53–1.73 (1989).

Schülein, "Cellulases of *Trichoderma reesei*" *Methods in Enzymology* 160:234–242 (1988).

Seiboth et al., "Disruption of the *Trichoderma reesei* cbh2 gene coding for cellobiohydrolase II leads to a delay in the triggering of cellulase formation by cellulose" *J. Gen. Microb.* 138:1259–1264 (1992).

Sheir–Neiss et al., "Characterization of the Secreted Celluloses of *Trichoderma reesei* Wild Type and Mutants During Controlled Fermentations" *Appl. Microbiol. Biotechnol.* 20:46–53 (1984).

Shoemaker et al., "Characterization and Properties of Cellulases Purified from *T. reesei* strain L27" *Bio/Technology* 687–690 (1983).

Shoemaker et al., "Molecular Cloning of Exo–cellobiohydrolase I Derived from *Trichoderma reesei* Strain L27" *Biotechnology* pp. 691–695 (1983).

Smith et al., "Sequence of the Cloned pyr4 Gene of *Trichoderma reesei* and its use as a Homologous Selectable Marker for Transformation" *Current Genetics* 19:27–33 (1991).

Stahl, U. et al., "Replication and expression of a bacterial–mitochondrial hybrid plasmid in the fungus *Podospora anserina*" *Proc. Natl. Acad. Sci. USA* 79:3641–3645 (1982).

Teeri et al., "Engineering Trichoderma and its cellulases *Trichoderma reesei* cellulase and cellobiohydrolase gene cloning and expression: potential strain improvement and enzyme engineering" *Trichoderma reesei Cellulases* pp. 156–167 (1990) [abstract].

Teeri et al., "Homologous domainsm in *Trichoderma reesei* cellulolytic enzymes: gene sequence and expression of cellobiohydrolase II" *Gene* 51:43–52 (1987).

Teeri, "The Cellulolytic Enzyme System of *Trichoderma reesei*" *VTT Publications* 38, pp. 1–52+Appendices 41 pps. (1987).

Tenkanen et al., "Two major xylanases of *Trichoderma–reesei*" *Enzyme Microb Technol.* 14(7):566–574 (1992).

Thomas, K., "Site–Directed Mutagenesis by Gene Targeting in Mouse Embryo–Derived Stem Cells" *Cell* 51:503–512 (Nov. 1987).

Toronnen et al. "The major xylanases of *Trichoderma reesei*: purification, and production of monoclonal antibodies" *Progress in Biotechnology* 7:501–504 (1992).

Toronnen et al., "The Two Major Xylanases from *Trichoderma reesei*: Characterization of Both Enzymes and Genes" *Bio/Technology* 10(11):1461–1465 (1992).

Tudzynski, P. et al., Transformation to senescence with plasmid–like DNA in the Ascomycete *Podospora anserina Current Genetics* 2:181–184 (1980).

Tyndall, R., "Improving the Softness and Surface Appearance of Cotton Fabrics and Garments by Treatment with Cellulase Enzymes" *Texile Chemist and Colorist* 24(6):23–26 (Jun. 1992).

U.S. Department of Health, Education and Welfare, Public Health Service, National Institutes of Health, "Modification of certified host–vector systems" *Recombinant DNA Technical Bulletin*, 2:132–134 (1979).

Ujile et al., "Low molecular weight xylanase from *Tricoderma viride* endo–1,4–beta–D–xylanases purification and characterization" *Appl. Env. Microb.* 57(6):1860–62 (1991) [Abstract].

Ulker et al., "Characterization of an Unglycosylatd Low Molecular Weight 1,4–β–glucan–glucanohydrolase of *Trichoderma reesei*" *FEMS Microbiology Letters* 69:215–219 (1990).

Ulrich, R.C. et al., "Transforming Basidiomycetes" *Molecular Genetics of Filamentous Fungi*: Alan R. Liss, Inc., pp. 39–57 (1985).

Uusitalo et al., "Enzyme Production by recombinant *Trichoderma reesei* strains" *Journal of Biotechnology* 17:35–50 (1991).

Van Arsdell et al., "Cloning, Characterization and Expression in *Saccharomyces cervisiae* of Endoglucananse I from *Trichoderma reesei*" *Bio/Technology*5:60–64 (1987).

Voragen et al., "Cellulases of a Mutant Strain of *Trichoderma viride* QM 9414", *Methods in Enzymology* 160:243–251 (1988).

Wilson et al., "Sequence of the *Aspergillus niger* pyrG Gene" *Nucl. Acids Res.* 16:2339 (1988).

Wilson et al., "Expression Vector pT7:TKII for the Synthesis of Authentic Biologically Active RNA Encoding Vaccinia Virus Thymidine Kinase" *Gene* 77:69–78 (1984).

Winnacker *From Genes to Clones Introduction to Gene Technology*, ed. Michael Weller, New York, New York 1987.

Wood, "Properties of Cellulolytic Enzyme Systems" *Biochem. Soc. Trans.* 13(2):407–410 (1985).

Wood et al., "The Mechanism of Fungal Cellulose Action" *Biochem J.* 260:37–43 (1989).

Wood et al., "Methods for Measuring Cellulase Activities" *Methods in Enzymology* 160:87–112 (1988).

Wood et al, "Aerobic and Anaerobic Fungal Cellulases, With Special Reference to Their Mode of Attack on Crystalline Cellulose" *Biochemistry and Genetics of Cellulose Degradation* pp. 31–52 (1988).

Wozney, "Using Purified Protein to Clone Its Gene" *Methods in Enzymology* 182:738–751 (1990).

Yamada et al., "Synthesis and Reaction of New Type I–N Ylide, N–tosyliminoiodinane" *Chem Letters* pp. 361–362 (1975).

Yamagishi, "Reforming of Cellulosic Fiber With Cellulose" *The Shizuoka Prefectural Hamamatsu, Textile Industrial Research Institute Report* 24:54–61 (1986).

Yang, et al., "Nucleotide sequence of a *Bacillus circulans* xylanase gene" *Nucleic Acids Res.* 16(14):7187.

Yanish–Perron et al., "Improved M13 phage cloning vectors and host strains:nucleotide sequences of the M13mp18 and pUC19 cecotrs" *Gene* 33:103–119 (1985).

Young, et al., "Efficient isolation of genes by using antibody probes" *Proc. Natl. Acad. Sci.* 80:1194–1198 (Mar. 1983).

Zappe, et al., Nucleotide sequence of a *Clostridium acetobutylicum* P262 xylanase gene (xynB).

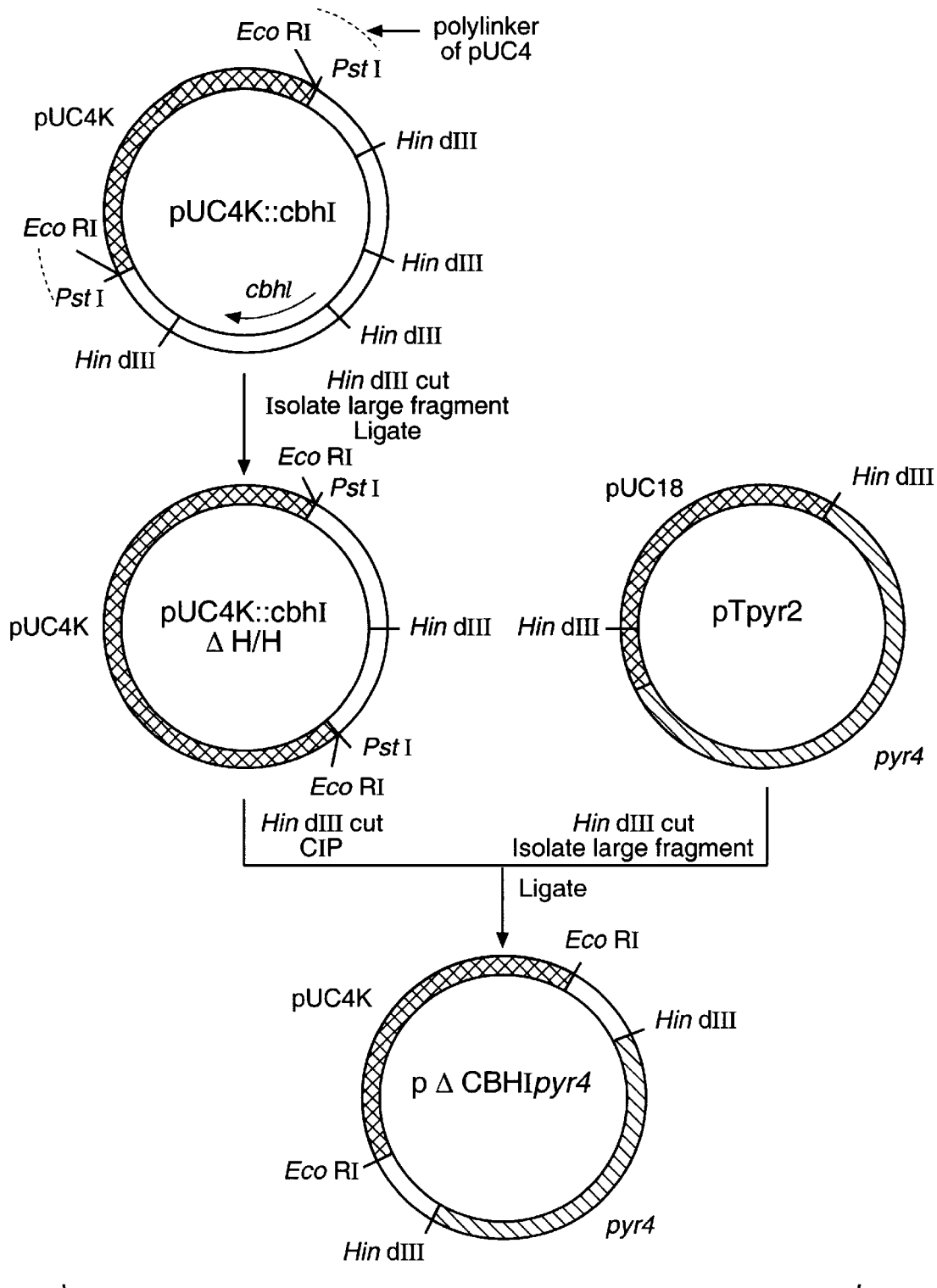
FIG._1

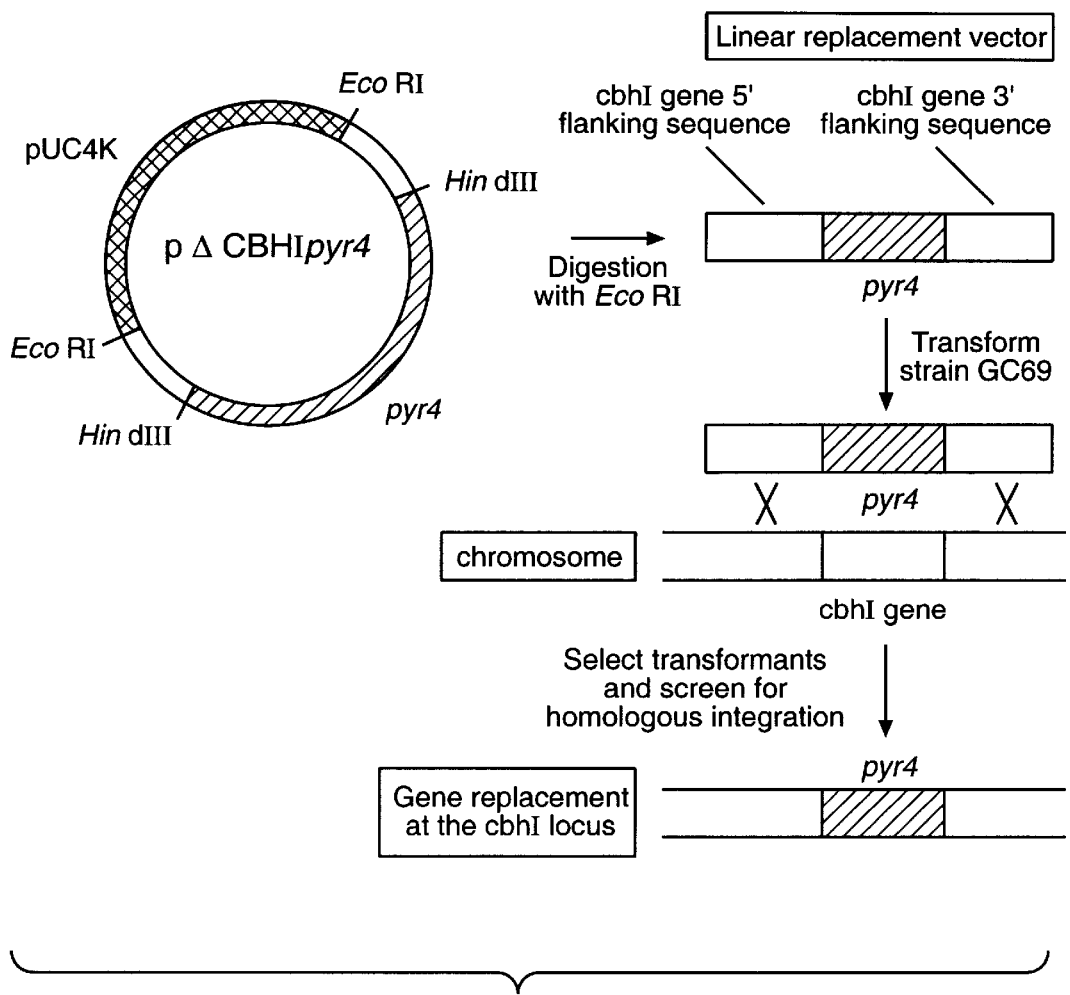
FIG._2

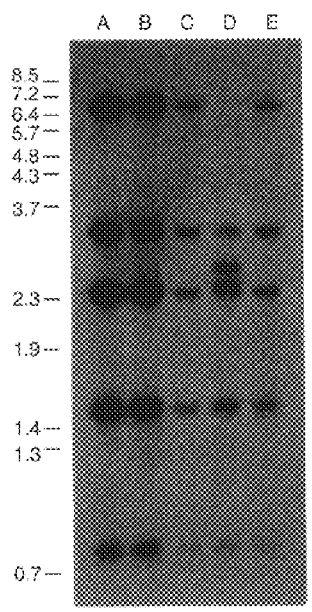 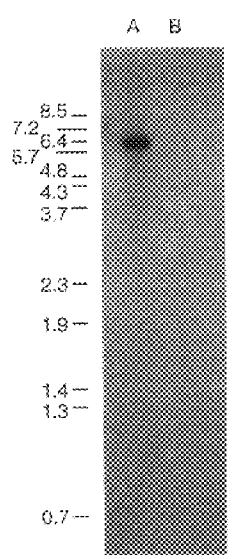 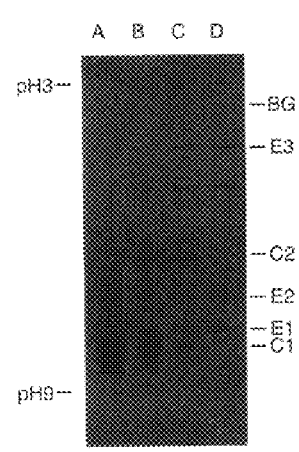 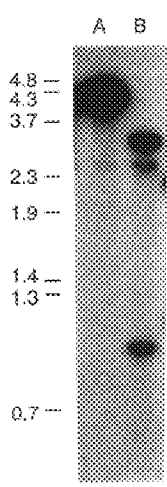
FIG._3    FIG._4    FIG._5    FIG._7

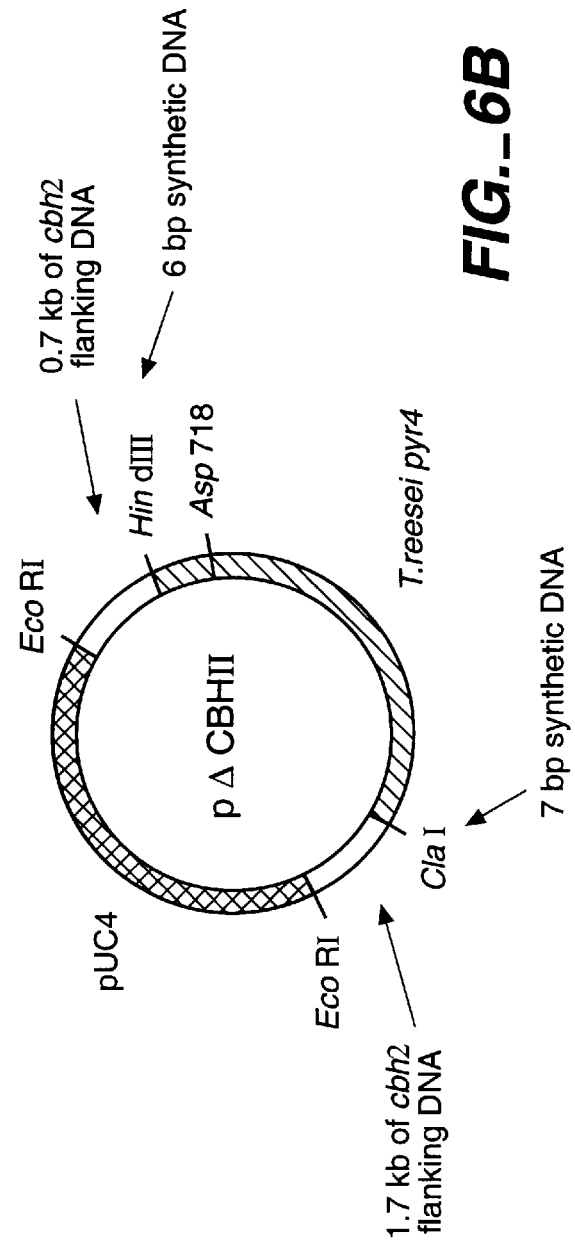
FIG._6A
FIG._6B

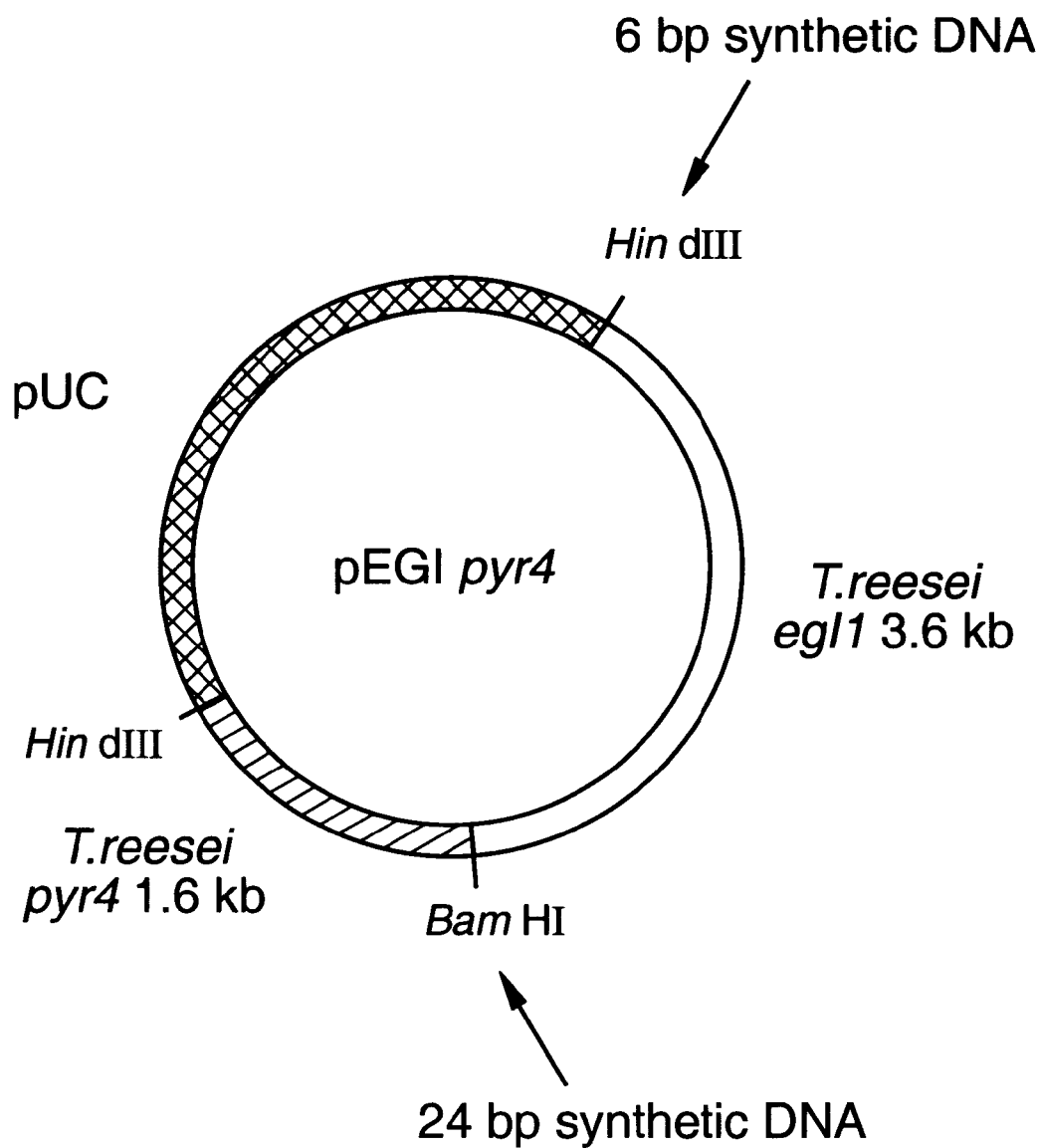
FIG._8

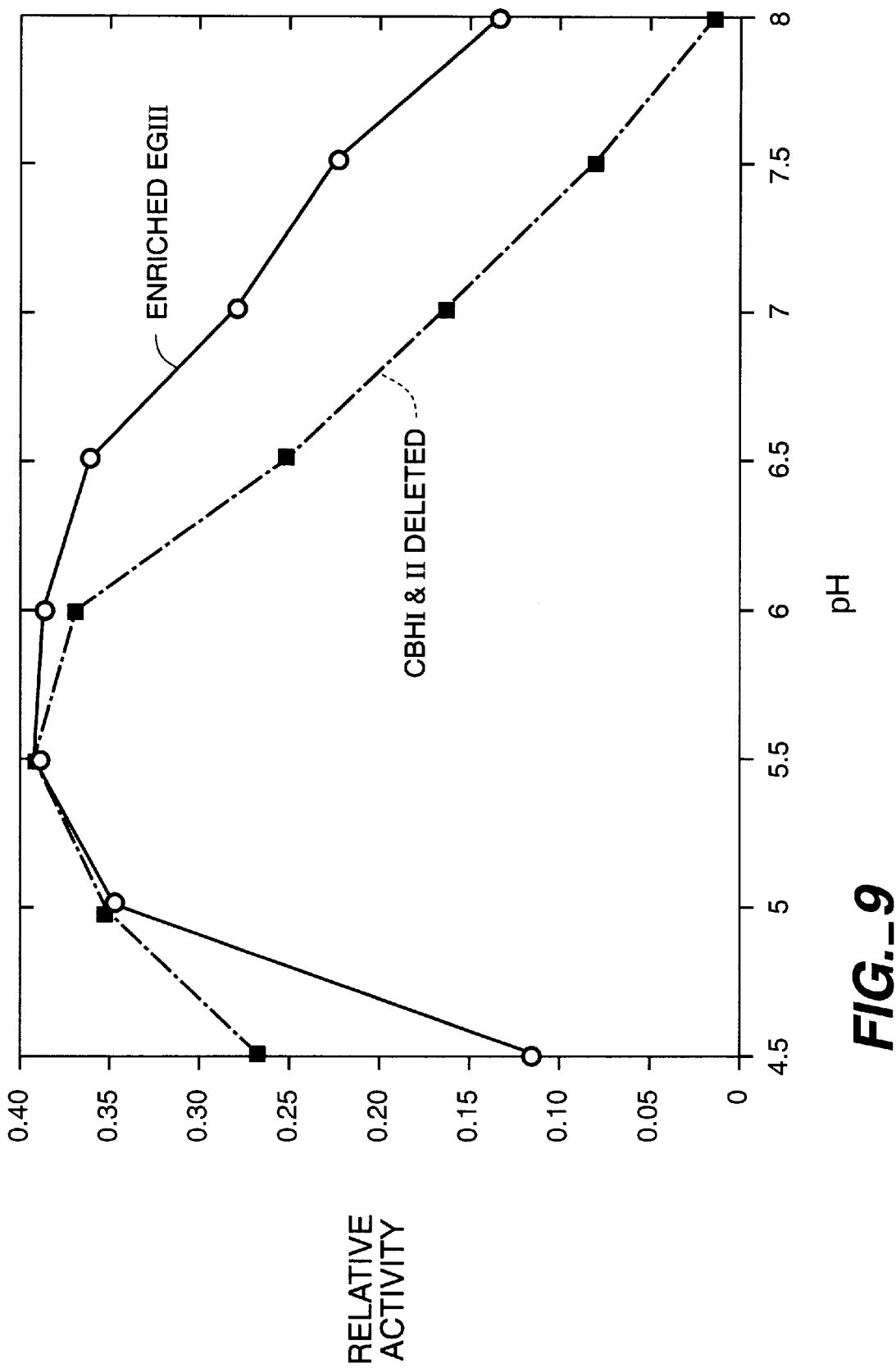
FIG._9

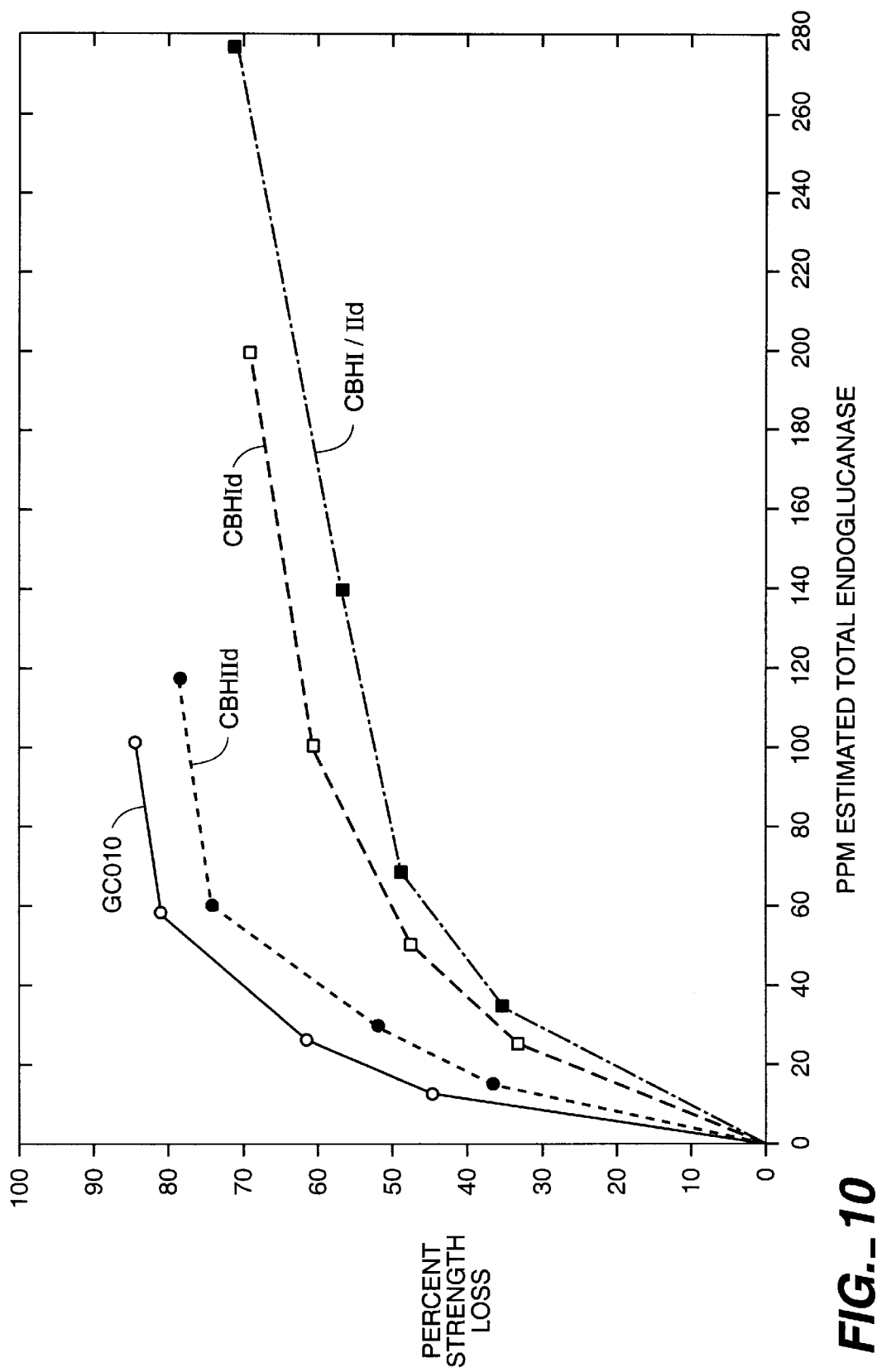
FIG._10

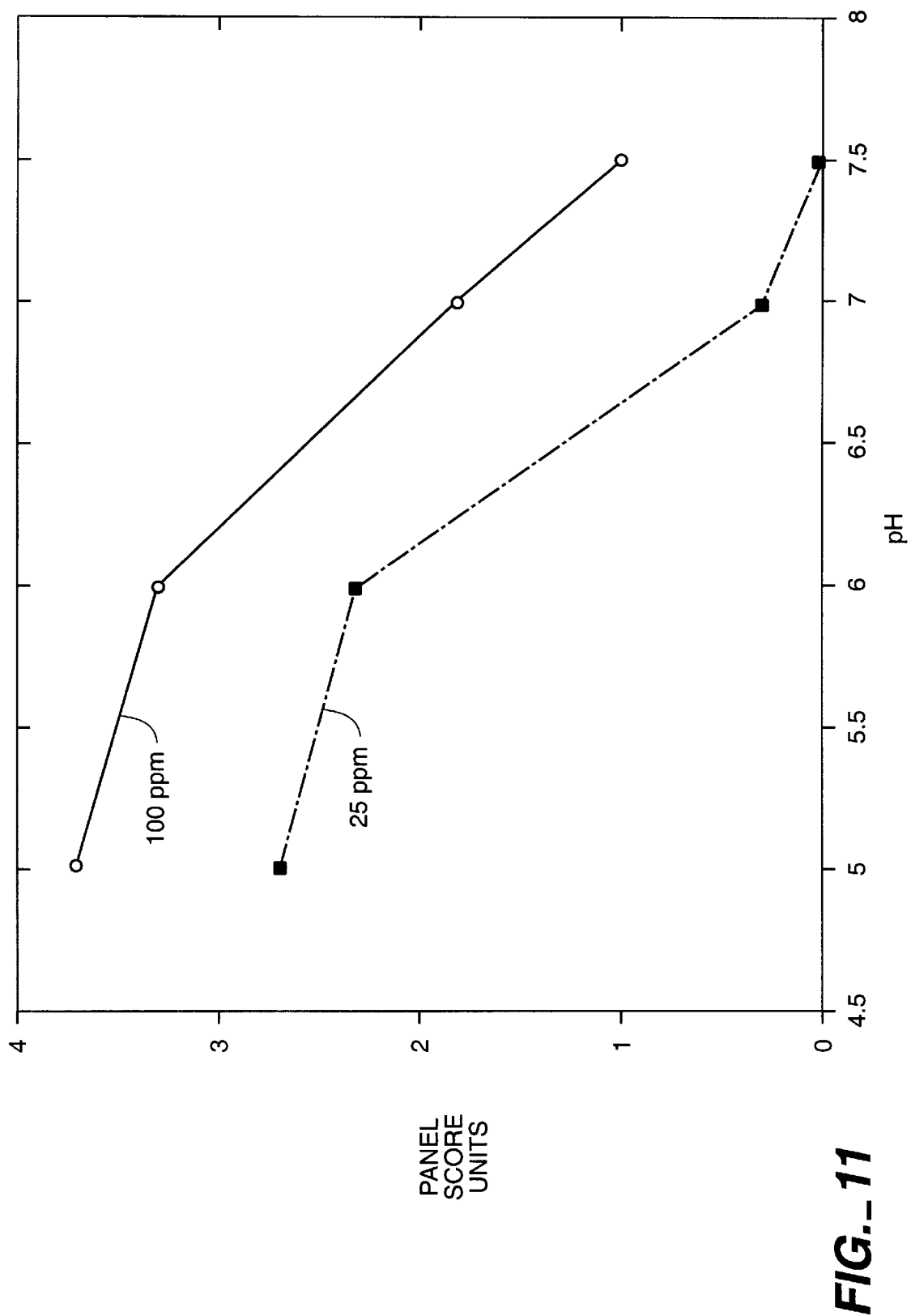
FIG._11

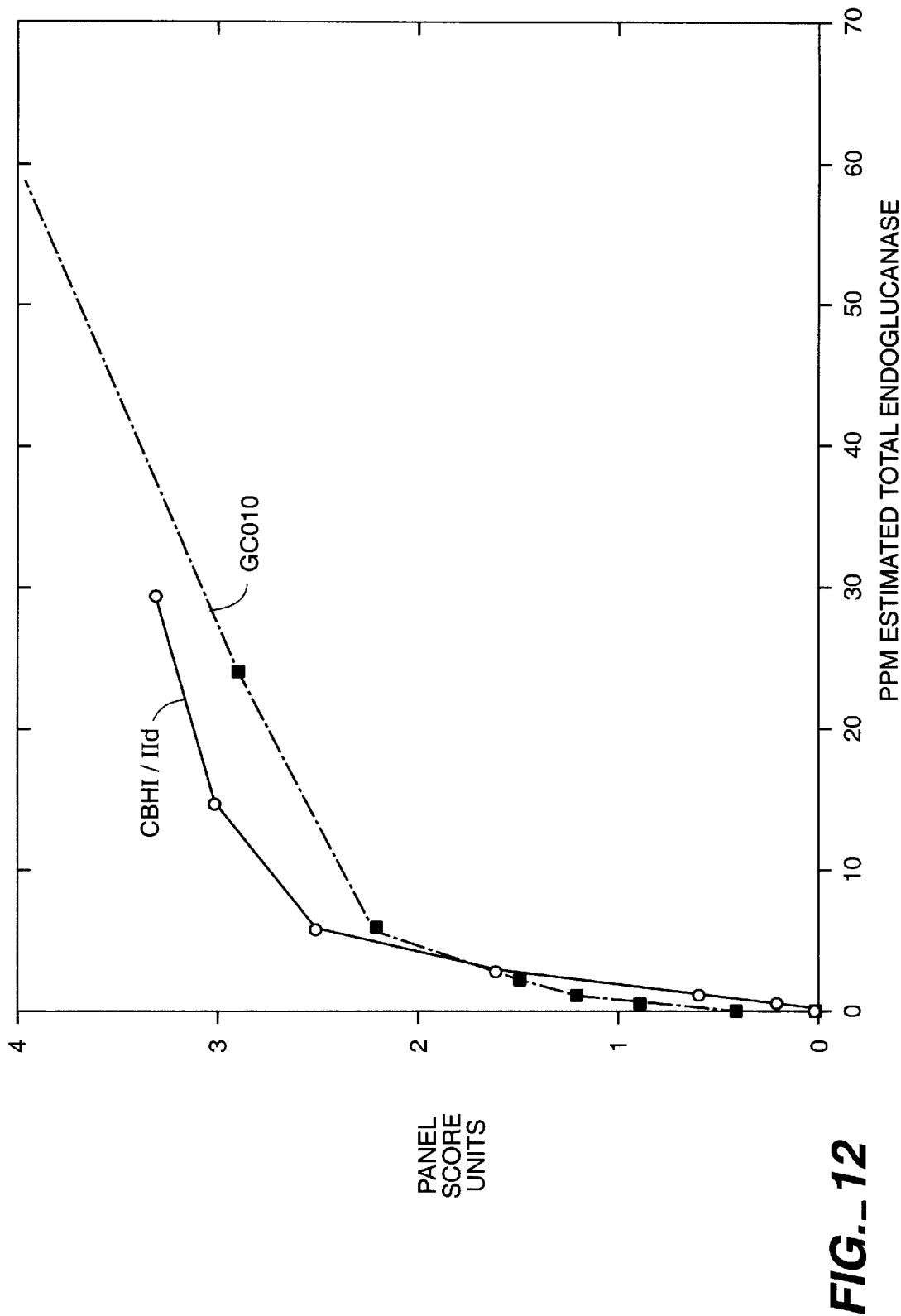
FIG._12

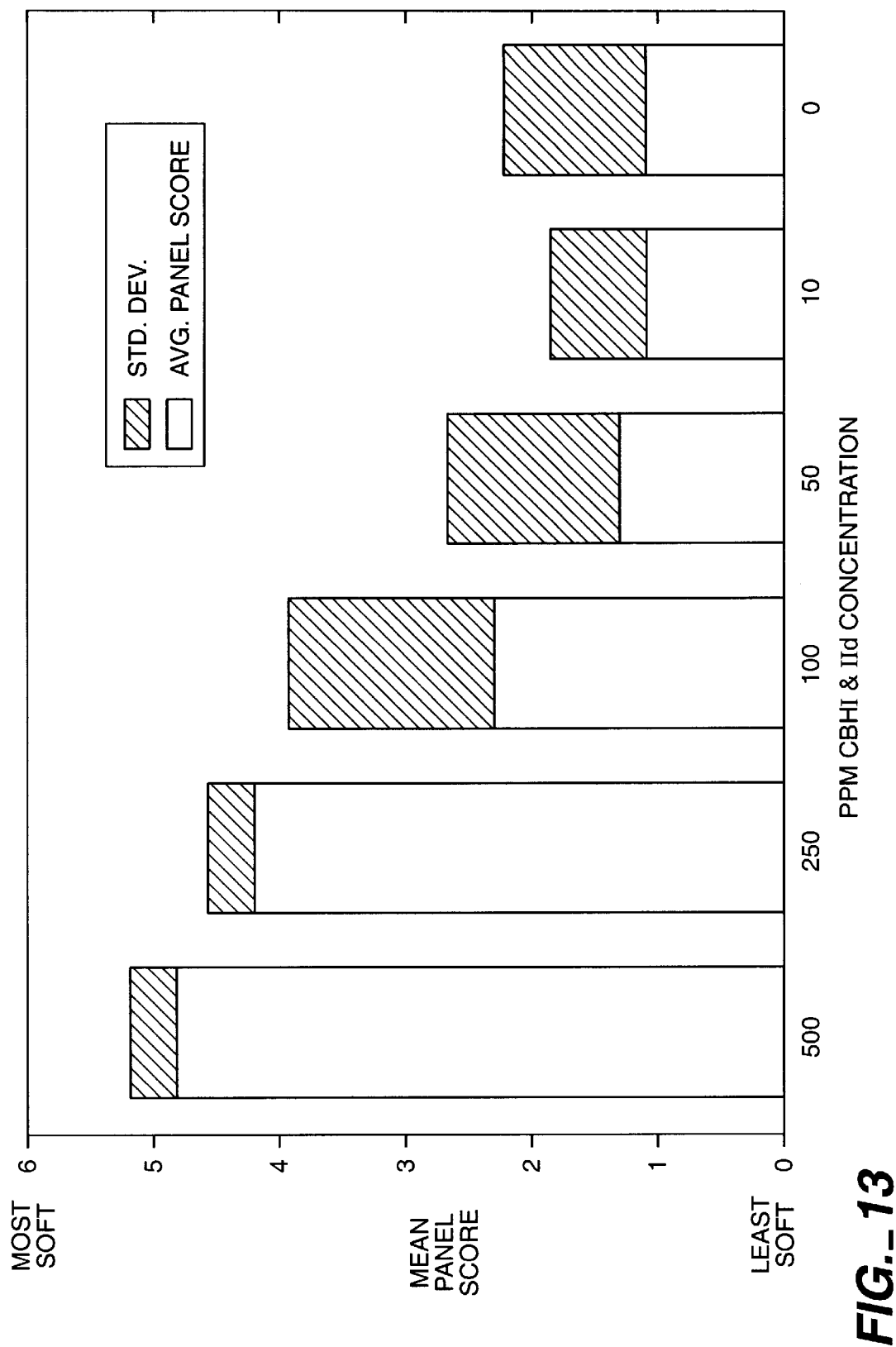
FIG._13

DETERGENT COMPOSITIONS CONTAINING CELLULASE COMPOSITIONS DEFICIENT IN CBH I TYPE COMPONENTS

This application is a continuation of application Ser. No. 08/152,099, filed Nov. 15, 1993, which is a continuation of application Ser. No. 07/713,738, filed Jun. 11, 1991, now abandoned, which is continuation-in-part of application Ser. No. 07/593,919, filed Oct. 5, 1990, now abandoned.

BACKGROUND OF THE INVENTION

1. Field of the Invention

The present invention is directed to detergent compositions containing specific cellulase compositions. In particular, the present invention is directed to detergent compositions containing (a) a cleaning effective amount of one or more surfactants and (b) a cellulase composition containing one or more endoglucanase (EG) type components and less than about 5 weight percent of exo-cellobiohydrolase (CBH) I type components and, preferably, less than about 5 weight percent of all CBH type components. Even more preferably, the cellulase compositions employed in the detergent compositions of this invention are free of all CBH I type components and preferably free of all CBH type components. Such detergent compositions provide improvements in softness, feel, color retention/restoration, and the like. Additionally, when such cellulase compositions contain some CBH I type components, although less than about 5 weight percent, an incremental cleaning benefit is also observed.

2. State of the Art

Cellulases are known in the art as enzymes that hydrolyze cellulose ($\beta$-1,4-glucan linkages) thereby resulting in the formation of glucose, cellobiose, cellooligosaccharides, and the like. While cellulases are produced (expressed) in fungi, bacteria and the like, those produced by fungi have been given the most attention because certain fungi produce a complete cellulase system capable of degrading crystalline forms of cellulose and such cellulases can be readily produced in large quantities via fermentation procedures.

In regard to the above, Schulein, "Methods in Enzymology", 160, 25, pages 234 et seq. (1988), discloses that certain fungi produce complete cellulase systems which are comprised of several different enzyme classifications including those identified as exo-cellobiohydrolases (EC 3.2.1.91) ("CBH"), endoglucanases (EC 3.2.1.4) ("EG"), and $\beta$-glucosidases (EC 3.2.1.21) ("BG"). On the other hand, some fungi are incapable of producing complete cellulase systems. Generally, these systems lack CBH components. See, for instance, Coughlan et al., Biochemistry and Genetics of Cellulose Degradation, Aubert et al., Editor, pages 11 et seq., (Academic Press, 1988); and Wood et al., Methods in Enzymology, 160, 25, pages 87 et seq., (Academic Press, New York, 1988).

Likewise, while bacterial cellulases are reported in the literature as containing little or no CBH components, there are a few cases where CBH-like components derived from bacterial cellulases have been reported to possess exo-cellobiohydrolase activity.

The fungal cellulase classifications of CBH, EG and BG can be further expanded to include multiple components within each classification. For example, multiple CBHs and EGs have been isolated from a variety of fungal sources including *Trichoderma longibrachiatum* which contains 2 CBHs, i.e. CBH I and CBH II, and at least 3 EGs, i.e., EG I, EG II and EG III.

The complete cellulase system comprising components from each of the CBH, EG and BG classifications is required to efficiently convert crystalline cellulose to glucose.

Isolated components are far less effective, if at all, in hydrolyzing crystalline cellulose. Moreover, a synergistic relationship is observed between the cellulase components particularly if they are of different classifications. That is to say the effectiveness of a complete cellulase system is significantly greater than the sum of the contributions from the isolated components of the same classification. In this regard, it is known in the art that the EG components and CBH components synergistically interact to more efficiently degrade cellulose. See, for example, Wood, Biochem. Soc. Trans., 13, pp. 407–410 (1985). The substrate specificity and mode of action of the different cellulase components varies significantly with classification which may account for the synergy of the combined components. For example, the current accepted mode of cellulase action is that endoglucanase components hydrolyze internal $\beta$-1,4-glucosidic bonds, particularly, in regions of low crystallinity of the cellulose and exo-cellobiohydrolase components hydrolyzes cellobiose from the non-reducing end of cellulose. The action of endoglucanase components greatly facilitates the action of exo-cellobiohydrolases by creating new chain ends which are recognized by exo-cellobiohydrolase components.

$\beta$-Glucosidase components act only on cellooligosaccharides, e.g., cellobiose, to give glucose as the sole product. They are considered an integral part of the cellulase system because they drive the overall reaction to glucose and thereby relieve the inhibitory effects of cellobiose on CBH and EG components.

On the other hand, cellulases are also known in the art to be useful in detergent compositions for the purposes of enhancing the cleaning ability of the composition, for use as a softening agent, and for improving the feel of cotton fabrics, and the like. While the exact mechanism by which cellulase compositions soften garments is not fully understood, softening and color restoration properties of cellulase have been attributed to alkaline endoglucanase components in cellulase compositions. Thus, for instance, International Application Publication No. WO 89/09259 discloses that detergent compositions containing a cellulase composition enriched in a specified alkaline endoglucanase component impart color restoration and improved softening to treated garments as compared to cellulase compositions not enriched in such a component. Additionally, the use of such alkaline endoglucanase components in detergent compositions complements the pH requirements of the detergent composition. The endoglucanase component of this reference is defined as one exhibiting maximal activity at an alkaline pH of 7.5 to 10 and which has defined activity criteria on carboxymethylcellulose and Avicel.

On the other hand, cellulase compositions are known in the art to degrade cotton-containing fabrics (see, for example, Suzuki et al., U.S. Pat. No. 4,822,516) which degradation is evidenced by reduced strength loss in the fabric. In turn, such strength loss accounts, in part, for the reluctance to the use of cellulase compositions in commercial detergent applications.

Accordingly, in view of the above, cellulase compositions containing one or more endoglucanase components which also provide reduced strength loss for cotton-containing fabrics as compared to a complete cellulase- system would be particularly advantageous for use in detergent compositions.

SUMMARY OF THE INVENTION

It has now been found that fungal cellulase compositions containing one or more endoglucanase type components can be combined in detergent compositions to impart improvements in softening, color retention/restoration and feel to cotton-containing fabrics washed in a wash medium containing such a composition. It has further been found that when such cellulase compositions contain less than about 5 weight percent of CBH I type components, the resulting detergent compositions impart less strength loss to the so-washed cotton-containing fabrics.

Accordingly, in one of its composition aspects, the present invention is directed to a detergent composition comprising (a) a cleaning effective amount of a surfactant or a mixture of surfactants and (b) from about 0.01 to about 5 weight percent, and preferably from about 0.05 to about 2 weight percent, of a fungal cellulase composition based on the weight of the detergent composition, wherein the fungal cellulase composition comprises one or more EG type components and less than about 5 weight percent of CBH I type components (based on total protein in the cellulase composition). In a preferred embodiment, the fungal cellulase composition employed in the detergent composition comprises one or more EG type components and less than about 5 weight percent of all CBH type components. Even more preferably, the fungal cellulase composition employed in this invention is free of all CBH I type components and, still more preferably, free of all CBH type components.

In another preferred embodiment, the cellulase composition is derived from a microorganism which has been genetically modified so as to be incapable of producing any CBH I type components and more preferably any CBH type components, i.e., CBH I type and CBH II type components. In even a more preferred embodiment, the cellulase composition is derived from a microorganism which has been genetically modified so as to be incapable of producing any CBH I type components or any CBH type components without the expression of any heterologous proteins.

In one of its method aspects, the present invention is directed to a strength-loss resistant method for enhancing the softness of a cotton-containing fabric which method comprises washing the fabric in a wash medium derived from a detergent composition comprising (a) a cleaning effective amount of a surfactant or a mixture of surfactants and (b) from about 0.01 to about 5, and preferably from about 0.05 to about 2, weight percent of a fungal cellulase composition based on the weight of the detergent composition wherein the cellulase composition comprises one or more EG type components and less than about 5 weight percent of CBH I type components based on the weight of protein in the cellulase composition.

In another of its method aspects, the present invention is directed to a strength loss resistant method for retaining/restoring the color of a cotton-containing fabric which method comprises washing the fabric one or more times in a wash medium derived from a detergent composition comprising (a) a cleaning effective amount of a surfactant or a mixture of surfactants and (b) from about 0.01 to about 5, and preferably from about 0.05 to about 2 weight percent of a fungal cellulase composition based on the weight of the detergent composition wherein the cellulase composition comprises one or more EG type components and less than about 5 weight percent of CBH I type components based on the weight of protein in the cellulase composition.

BRIEF DESCRIPTION OF THE DRAWINGS

FIG. 1 is an outline of the construction of pΔCBHIpyr4.

FIG. 2 illustrates deletion of the *Trichoderma longibrachiatum* cbh1 gene by integration of the larger EcoRI fragment from pΔCBHIpyr4 at the cbh1 locus on one of the *Trichoderma longibrachiatum* chromosomes.

FIG. 3 is an autoradiograph of DNA from a *Trichoderma reesei* strain GC69 transformed with EcoRI digested pΔCBHIpyr4 after Southern blot analysis using a $^{32}P$ labelled pΔCBHIpyr4 as the probe.

FIG. 4 is an autoradiograph of DNA from a *Trichoderma longibrachiatum* strain GC69 transformed with EcoRI digested pΔCBHIpyr4 after Southern blot analysis using a $^{32}P$ labelled pIntCBHI as the probe.

FIG. 5 is an isoelectrofocusing gel displaying the proteins secreted by the wild type and by transformed strains of *Trichoderma longibrachiatum*. Specifically, in FIG. 5,, Lane A of the isoelectric focusing gel employs partially purified CBH I from *Trichoderma longibrachiatum*; Lane B employs protein from a wild type *Trichoderma longibrachiatum*; Lane C employs protein from a *Trichoderma reesei* strain with the cbh1 gene deleted; and Lane D employs protein from a *Trichoderma reesei* strain with the cbh1 and cbh2 genes deleted.

In FIG. 5, the right hand side of the figure is marked to indicate the location of the single proteins found in one or more of the secreted proteins. Specifically, BG refers to β-glucosidase; E1 refers to endoglucanase I; E2 refers to endoglucanase II; E3 refers to endoglucanase III; Cl refers to exo-cellobiohydrolase I; and C2 refers to exo-cellobiohydrolase II.

FIG. 6A is a representation of the *Trichoderma longibrachiatum* cbh2 locus cloned as a 4.1 kB EcoRI fragment of genomic DNA and FIG. 6B is a representation of the cbh2 gene deletion vector, pPΔCBHII.

FIG. 7 is an autoradiograph of DNA from a *Trichodernna longibrachiatum* strain P37PΔCBHI transformed with EcoRI digested pPΔCBHII after Southern blot analysis using a $^{32}P$ labelled pPΔCBHII as the probe.

FIG. 8 is a diagram of the plasmid pEGIpyr4.

FIG. 9 illustrates the RBB-CMC activity profile of an EG enriched fungal cellulase composition (CBH I and II deleted) derived from *Trichoderma longibrachiatum* over a pH range at 40° C.; as well as the activity profile of an enriched EG III cellulase composition derived from *Trichoderma longibrachiatum* over a pH range at 40° C.

FIG. 10 illustrates strength loss results after three wash cycles in a launderometer for cotton-containing fabrics treated with cellulase compositions having varying amounts of CBH components.

FIG. 11 illustrates fiber removal results (based on panel test scores) for cotton-containing fabrics treated with cellulase secreted by a wild type *Trichoderma longibrachiatum* (whole cellulase) at various pHs.

FIG. 12 illustrates fiber removal results (based on panel test scores) for cotton-containing fabrics treated with varying concentrations (in ppm) of cellulase secreted by a wild type *Trichoderma longibrachiatum* and for a cotton fabric treated with cellulase secreted by a strain of *Trichoderma longibrachiatum* genetically engineered so as to be incapable of secreting CBH I and CBH II.

FIG. 13 illustrates the softness panel test results for varying concentrations (in ppm) of an EG enriched cellulase composition derived from a strain of *Trichoderma longibrachiatum* genetically modified so as to be incapable of producing CBH I and II.

DETAILED DESCRIPTION OF THE INVENTION

As noted above, the present invention generally relates to detergent compositions containing fungal cellulase compositions containing one or more EG type cellulase components and less than about 5 weight percent of CBH I type components as well as for methods employing such cellulase compositions. When used in wash media having acidic, neutral or alkaline pH's, such detergent compositions impart improvements in softening, color retention/restoration, and feel to cotton-containing fabrics washed in such media. Moreover, because of the small amount of CBH I type components present in the cellulase composition, these compositions also provide reduced strength loss as compared to those compositions containing greater amounts of CBH I type components.

However, prior to discussing this invention in detail, the following terms will first be defined.

The term "fungal cellulase" refers to an enzyme composition derived from fungal sources or microorganisms genetically modified so as to incorporate and express all or part of the cellulase genes obtained from a fungal source. Fungal cellulases act on cellulose or one or more of its degradation products to hydrolyze cellulose and give primary products, glucose and cellobiose. Fungal cellulases are distinguished from cellulases produced from non-fungal sources including microorganisms such as actinomycetes, gliding bacteria (myxobacteria) and true bacteria. Fungi capable of producing cellulases useful in preparing cellulase compositions used in the detergent compositions described herein are disclosed in British Patent No. 2 094 826A, the disclosure of which is incorporated herein by reference.

Most fungal cellulases generally have their optimum activity in the acidic or neutral pH range although some fungal cellulases are known to possess significant activity under neutral and slightly alkaline conditions, i.e., for example, cellulase derived from *Humicola insolens* is known to have activity in neutral to slightly alkaline conditions.

Fungal cellulases are known to be comprised of several enzyme classifications having different substrate specificity, enzymatic action patterns, and the like. Additionally, enzyme components within each classification can exhibit different molecular weights, different degrees of glycosylation, different isoelectric points, different substrate specificity, different enzymatic action patterns, etc. For example, fungal cellulases can contain cellulase classifications which include endoglucanases (EGs), exo-cellobiohydrolases (CBHs), β-glucosidases (BGs), etc. On the other hand, while bacterial cellulases are reported in the literature as containing little or no CBH components, there are a few cases where CBH-like components derived from bacterial cellulases have been reported to possess exo-cellobiohydrolase activity.

A fungal cellulase composition produced by a naturally occurring fungal source and which comprises one or more CBH and EG components wherein each of these components is found at the ratio produced by the fungal source is sometimes referred to herein as a "complete fungal cellulase system" or a "complete fungal cellulase composition" to distinguish it from the classifications and components of cellulase isolated therefrom, from incomplete cellulase compositions produced by bacteria and some fungi, or from a cellulase composition obtained from a microorganism genetically modified so as to overproduce, underproduce or not produce one or more of the CBH and/or EG components of cellulase., The fermentation procedures for culturing fungi for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

"Endoglucanase ("EG") type components" refer to all of those fungal cellulase components or combination of components which exhibit detergent activity properties similar to the endoglucanase components of *Trichoderma longibrachiatum*. In this regard, the endoglucanase components of *Trichoderma longibrachiatum* (specifically, EG I, EG II, EG III, and the like either alone or in combination) impart softening, color retention/restoration and improved feel to cotton-containing fabrics when these components are incorporated into a wash medium and the fabric is treated with this medium. Accordingly, endoglucanase type components are those fungal cellulase components which impart softening, color retention/restoration and improved feel to cotton garments when these components are incorporated into a wash medium. In a preferred embodiment, the endoglucanase type components employed in the detergent compositions of this invention also impart less strength loss to cotton-containing fabrics as compared to strength loss arising from the complete cellulose system derived from *Trichoderma longibrachiatum*.

Such endoglucanase type components may not include components classified as endoglucanases using traditional biochemical activity tests. For example, such traditional activity tests are based on the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid swollen cellulose (e.g., Walseth cellulose) and hydrolyze less readily the more highly crystalline forms of cellulose (e.g., Avicel, Solkafloc, etc.). In contrast, it is believed that not all endoglucanase components, as defined by such activity tests, will provide improved softness, feel and color retention/restoration. Accordingly, it is more accurate for the purposes herein to define endoglucanase type components as those components of fungal cellulase which possess similar properties in detergent compositions as possessed by the endoglucanase components, of *Trichoderma longibrachiatum*.

Fungal cellulases can contain more than one EG type component. The different components generally have different isoelectric points, different molecular weights, different degrees of glycosylation, different substrate specificity, different enzymatic action patterns, etc. The different isoelectric points of the components allow for their separation via ion exchange chromatography and the like. In fact, the isolation of components from different fungal sources is known in the art. See, for example, Bjork et al., U.S. Ser. No. 07/686,265 (now U.S. Pat. No. 5,120,463) which is a continuation of U.S. Ser. No. 07/422,814 which is now abandoned, Schulein et al., International Application WO 89/09259, Wood et al., Biochemistry and Genetics of Cellulose Degradation, pp. 31 to 52 (1988); Bhat et al., Carbohydrate Research, Vol. 190, pp. 279 to 297 (1989); Schulein, Methods in Enzymology, Vol. 160, pp. 234 to 242 (1988); and the like. The entire disclosure of each of these references is incorporated herein by reference.

In general, it is contemplated that combinations of EG type components may give a synergistic response in improving softening, color retention/restoration and feel as compared to a single EG type component. On the other hand, a single EG type component may be more stable or have a broader spectrum of activity over a range of pHs. Accordingly, the EG type components employed in this invention can be either a single EG type component or a combination of two or more EG type components. When a combination of components is employed, the EG type components may be derived from the same or different fungal sources.

"Exo-cellobiohydrolase type ("CBH type") components" refer to those fungal cellulase components which exhibit detergent activity properties similar to CBH I and/or CBH II components of *Trichoderma longibrachiatum*. In this regard, when used in the absence of EG type components (as defined above), the CBH I and CBH II components of *Trichoderma longibrachiatum* alone do not impart significant color retention/restoration and improved feel to the so-treated cotton-containing fabrics. Additionally, when used in combination with EG type components, the CBH I component of *Trichoderma longibrachiatum* imparts enhanced strength loss and an incremental cleaning effect to cotton-containing fabrics.

Accordingly, CBH I type components and CBH II type components refer to those fungal cellulase components which exhibit detergent activity properties similar to CBH I and CBH II components of *Trichoderma longibrachiatum*, respectively. As noted above, for CBH I type components, this includes the properties of enhancing strength loss of cotton-containing fabrics and/or imparting an incremental cleaning benefit when used in 'the presence of EG type components. In a preferred embodiment, the CBH I components also impart an incremental softening benefit when used in the presence of EG type components.

Such exo-cellobiohydrolase type components may include components not traditionally classified as exo-cellobiohydrolases using activity tests such as those used to characterize CBH I and CBH II from *Trichoderma longibrachiatum*. For example, using such traditional classification tests, such components are: (a) competitively inhibited by cellobiose ($K_i$ approximately 1 mM); (b) unable to hydrolyze to any significant degree substituted celluloses, such as carboxymethylcellulose, etc., and (c) able to hydrolyze phosphoric acid swollen cellulose and to a lesser degree highly crystalline cellulose. In contrast, it is believed that some fungal cellulase components which are characterized as CBH components by such activity tests, will provide improved softness, feel and color retention/restoration to cotton-containing fabrics when these components are used alone in detergent compositions. Accordingly, it is believed to be more accurate for the purposes herein to define such exo-cellobiohydrolases as EG type components because these components possess similar functional properties in detergent compositions as possessed by the endoglucanase components of *Trichoderma longibrachiatum*.

Fungal cellulases enriched in EG type components can be obtained by purification techniques. Specifically, the complete cellulase system can be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient.

It is also contemplated that mixtures of cellulase components having the requisite ratio of EG type components to CBH I type cellulase components could be prepared by means other than isolation and recombination of the components. In this regard, it may be possible to modify the fermentation conditions for a natural microorganism in order to give relatively high ratios of EG to CBH components. Likewise, recombinant techniques can alter the relative ratio of EG components to CBH components so as to produce a mixture of cellulase components having a relatively high ratio of EG components to CBH components or which can produce one or more EG components free of all CBH components. In regard to the above, a preferred method for the preparation of cellulase compositions enriched in EG type components is by genetically modifying a microorganism so as to be incapable of producing one or more CBH type components which methods do not produce any heterologous protein. Likewise, it is also possible to genetically modify a microorganism so as to overproduce one or more EG type components. For example, U.S. Ser. No. 07/593,919, filed Oct. 5, 1990 and which is incorporated herein by reference in its entirety, discloses methods for genetically engineering *Trichoderma longibrachiatum* so as to be incapable of producing one or more CBH components and/or overproducing one or more EG components. Moreover, the methods of that application create *Trichoderma longibrachiatum* strains which do not produce any heterologous proteins. Likewise, Miller et al., "Direct and Indirect Gene Replacement in *Aspergillus nidulans*", Molecular and Cellular Biology, p. 1714–1721 (1985) discloses methods for deleting genes in *Aspergillus nidulans* by DNA mediated transformation using a linear fragment of homologous DNA. The methods of Miller et al., would achieve gene deletion without producing any heterologous proteins.

In view of the above, the deletion of the genes responsible for producing either CBH I type or CBH II type cellulase components would have the effect of enriching the amount of EG type components present in the cellulase composition. Likewise, the deletion of those genes responsible for producing CBH I and II type components would result in a cellulase composition free of CBH type components.

It is still further contemplated that fungal cellulase compositions can be used herein from fungal sources which produce an incomplete fungal cellulase composition. For example, it is known that certain fungi produce cellulases compositions free of CBH components. See, for example, Coughlan et al., Biochemistry and Genetics of Cellulose Degradation, Aubert et al. Editors, pp. 11–30 (Academic Press, 1988), disclose that brown rot fungi do not apparently produce CBH components, but it may be possible that one or more of these components are CBH I type components. On the other hand, if a sufficient amount of the endoglucanases produced by such fungi are, for the purposes herein, EG type components, then it would be possible to use such cellulase in the practice of this invention without enrichment to obtain the necessary ratio of EG type components to CBH I type components.

Additionally, a requisite amount of one or more CBH type components purified by conventional procedures can be added to a cellulase composition produced from a microorganism genetically engineered so as to be incapable of producing CBH type components so as to achieve a specified ratio of EG type components to one or more CBH type components, i.e., a cellulase composition free of all CBH type components so as to be enriched in EG type components can be formulated to contain 1 weight percent of a CBH I type component merely by adding this amount of a purified CBH I type component to the cellulase composition.

"β-Glucosidase (BG) components" refer to those components of cellulase which exhibit BG activity; that is to say that such components will act from the non-reducing end of cellobiose and other soluble cellooligosaccharides, ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and thus are often called aryl-glucosidases. It should be noted that not all aryl-glucosidases are BG components, in that some do not hydrolyze cellobiose.

It is contemplated that the presence or absence of BG components in the cellulase composition can be used to regulate the activity of the CBH components. Specifically, because cellobiose is produced during cellulose degradation by CBH components, and because high concentrations of cellobiose are known to inhibit CBH activity, and further because such cellobiose is hydrolyzed to glucose by BG components, the absence of BG components in the cellulase composition will "turn-off" CBH activity when the concentration of cellobiose reaches inhibitory levels. It is also contemplated that one or more additives (e.g., cellobiose, glucose, etc.) can be added to the cellulase composition to effectively "turn-off", directly or indirectly, some or all of the CBH I type activity as well as other CBH activity. When such additives are employed, the resulting composition is considered to be a composition suitable for use in this invention if the amount of additive employed is sufficient to lower the CBH I type activity to levels equal to or less than the CBH I type activity levels achieved by using the cellulase compositions described herein.

On the other hand, a cellulase composition containing added amounts of BG components may increase overall hydrolysis of cellulose if the level of cellobiose generated by the CBH components becomes restrictive of such overall hydrolysis in the absence of added BG components.

Methods to either increase or decrease the amount of BG components in the cellulase composition are disclosed in U.S. Ser. No. 07/625,140, filed Dec. 10, 1990, as attorney docket no. 010055-056 and entitled "SACCHARIFICATION OF CELLULOSE BY CLONING AND AMPLIFICATION OF THE β-GLUCOSIDASE GENE OF *TRICHODERMA longibrachiatum*", which application is incorporated herein by reference.

Fungal cellulases can contain more than one BG component. The different components generally have different isoelectric points which allow for their separation via ion exchange chromatography and the like. Either a single BG component or a combination of BG components can be employed.

When employed in the detergent composition, the BG component is generally added in an amount sufficient to prevent inhibition of the CBH and EG components and particularly, CBH I type cellulase components, by cellobiose. The amount of BG component added depends upon the amount of cellobiose produced in the detergent wash which can be readily determined by the skilled artisan. However, when employed, the weight percent of BG component relative to CBH type components in the cellulase composition is preferably from about 0.2 to about 10 weight percent, and more preferably, from about 0.5 to about 5 weight percent.

Preferred fungal cellulases for use in preparing the fungal cellulase compositions used in this invention are those obtained from *Trichoderma longibrachiatum, Trichoderma koningii,* Pencillum sp., *Humicola insolens*, and the like. Certain fungal cellulases are commercially available, i.e., CELLUCAST (available from Novo Industry, Copenhagen, Denmark), RAPIDASE (available from Gist Brocades, N.V., Delft, Holland), CYTOLASE 123 (available from Genencor International, South San Francisco, Calif.) and the like. Other fungal cellulases can be readily isolated by art recognized fermentation and isolation procedures.

The term "cotton-containing fabric" refers to sewn or unsewn fabrics made of pure cotton or cotton blends including cotton woven fabrics, cotton knits, cotton denims, and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), polyester fibers (for example, polyethylene terephthalate), polyvinyl alcohol fibers (for example, Vinylon), polyvinyl chloride fibers, polyvinylidene chloride- fibers, polyurethane fibers, polyurea fibers and aramid fibers. It is contemplated that regenerated cellulose, such as rayon, could be used as a substitute for cotton in cotton-containing fabrics.

The term "surface active agent or surfactant" refers to anionic, non-ionic and ampholytic surfactants well known for their use in detergent compositions.

The term "wash medium" refers to an aqueous wash solution prepared by adding a requisite amount of a detergent (surfactant) composition to water. The wash medium generally contains a cleaning effective amount of the detergent.

The wash medium is defined as an "acidic wash medium" if the pH of the medium is from about 4 to less than about 7. The wash medium is defined as a "neutral wash medium" if the pH of the medium is about 7. The wash medium is defined as an "alkaline wash medium" if the pH of the medium is from above 7 to about 10. Preferably, the alkaline wash medium will have a pH of from above 7 to about 9 and, even more preferably, from above 7 to about 8.

The present invention is directed to the discovery that EG type components can be used in detergent compositions to effect softening as well as color retention/restoration and feel of cotton-containing fabrics regardless of whether such compositions are employed in an acidic, neutral or alkaline wash medium. However, because detergent compositions are generally employed in alkaline conditions, the cellulase composition employed is preferably one which possesses some activity under such conditions. Preferred cellulase compositions include those derived from *T. longibrachiatum* and *Humicola insolens*. Cellulase compositions from *Humicola insolens* are known in the art to retain significant activity under alkaline conditions.

Although the presence of EG type components are necessary to effect color retention/restoration, softening and improved feel, specified mixtures of EG type components and CBH type components (including CBH I type components) also show the same benefits or even some incremental benefits. Specifically, while the use of EG components will result in some cleaning benefit, an incremental cleaning benefit is observed for cotton-containing fabrics washed with a detergent composition containing a cellulase composition containing one or more EG type components and which contains CBH I type cellulase components. Additionally, while the use of EG components will effect softening, an incremental softening benefit may be achieved by incorporating some CBH I type components with the EG type components.

On the other hand, the presence of significant amounts of CBH I type components in combination with the EG type. components results in enhanced strength loss to cotton-containing fabrics compared to cellulase compositions which are either free of CBH I type components or contain reduced amounts of CBH I type components. Accordingly, in order to minimize the strength loss characteristics of cellulase containing detergent compositions, the detergent compositions of the present invention employ cellulase compositions containing one or more EG type components and less than about 5 weight percent, and preferably less than about 2 weight percent, of CBH I type components. Detergent compositions containing such cellulase compositions provide the desired enhancements to the cotton-containing fabrics while providing for reduced strength loss as compared to detergent compositions containing a cellulase composition which has greater amounts of CBH I type components.

Further in regard to the above, the selection of the specific cellulase composition for use in the detergent composition of this invention is made by balancing the desire for an incremental cleaning benefit achieved by the presence of some CBH I type components against that for strength loss resistance which dictates the use of minimal or no CBH I type components. That is to say that if the primary emphasis for incorporating cellulase into the detergent composition is for improved softness, color retention/restoration, and improved feel of cotton-containing fabrics with the minimum possible strength loss to the cotton-containing fabric, then the cellulase employed in the detergent composition should preferably comprise one or more EG type components free of all CBH I type components.

On the other hand, if the primary emphasis for incorporating cellulase into the detergent composition is for color retention/restoration, improved softness and improved feel of cotton-containing fabrics, in conjunction with an incremental cleaning benefit, then the cellulase employed in the detergent composition should contain a cellulase comprising one or more EG type components as well as some CBH I type component (albeit less than about 5 weight percent, preferably less than about 2 weight percent, based on the total protein weight of the cellulase composition).

In regard to the above, the amount of cellulase generally employed in the detergent compositions of this invention is an amount sufficient to impart color retention/restoration and softness to the cotton garments. Preferably, the cellulase compositions are employed from about 0.01 weight percent to about 5 weight percent relative to the weight of the total detergent composition. More preferably, the cellulase compositions are employed from about 0.05 weight percent to about 2 weight percent relative to the weight of the total detergent composition. The specific concentration of cellulase employed in the detergent composition is selected so that upon dilution into a wash medium, the concentration of EG type components will range from about 0.5 to about 500 ppm, and preferably from about 2 to about 100 ppm. The specific amount of cellulase employed in the detergent composition will depend on the amount of EG type components in the cellulase compositions as well as the extent the detergent composition will be diluted upon addition to water to form a wash medium. These factors are readily ascertained by the skilled artisan.

Preferably, the cellulase compositions employed in the detergent compositions of this invention contain at least about 20 weight percent of endoglucanase type components based on the total weight of protein in the cellulase composition, more preferably, at least about 50 weight percent, and even more preferably, at least about 70 weight percent, and most preferably, at least about 90 weight percent of endoglucanase type components based on the total weight of protein in the cellulose composition.

At lower cellulase concentrations (i.e., concentrations of EG type components of less than about 5 ppm in the wash medium), softness, color retention/restoration and improved feel achieved by use of the detergent compositions of this invention is more evident over repeated washings. At higher concentrations (i.e., concentrations of EG type components of about 5 ppm and above in the wash medium), the improvements can become noticeable in a single wash.

One of the important aspects of the present invention is that by tailoring the cellulase composition to contain one or more EG components and to contain minimal amounts of CBH I type components, it is possible to achieve the desired effects of softening, color retention/restoration and improved feel while reducing strength loss to the cotton-containing fabric.

Additionally, the use of such tailored cellulase compositions permits the use of lower concentrations of cellulase in the detergent composition. In turn, the use of lower concentrations of cellulase in the detergent compositions should lead to improved consumer safety.

The cellulase composition as described above can be added to the detergent composition either in a liquid diluent, in granules, in emulsions, in gels, in pastes, and the like. Such forms are well known to the skilled artisan. When a solid detergent composition is employed,, the cellulase composition is preferably formulated as granules. Preferably, the granules can be formulated so as to contain a cellulase protecting agent. See, for instance, U.S. Ser. No. 07/642,669 filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granules can be formulated so as to contain materials to reduce the rate of dissolution of the granules into the wash medium. Such materials and granules are disclosed in U.S. Ser. No. 07/642,596 filed on Jan. 17, 1991 as Attorney Docket No. GCS-171-US1 and entitled "GRANULAR COMPOSITIONS" which application is incorporated herein by reference in its entirety.

The detergent compositions of this invention employ a surface active agent, i.e., surfactant, including anionic, nonionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and. potassium; alkaline earth metal ions such as calcium and, magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Suitable surfactants for use in this invention are disclosed in British Patent Application No. 2 094 826 A, the disclosure of which is incorporated herein by reference.

Mixtures of such surfactants can also be used.

The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. Upon dilution in the wash medium, the surfactant concentration is generally about 500 ppm or more; and preferably, from about 1000 ppm to 15,000 ppm.

In addition to the cellulase composition and the surfactant(s), the detergent compositions of this invention can optionally contain one or more of the following components:

Hydrolases except cellulase

Such hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and α-aminoacylpeptide hydrolase, peptidyl-amino acid hydrolase, acylamino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B. urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function intacid to neutral systems, but one which is obtained from bacteria exhibits high activity in an alkaline system; (3) carboxylate ester hydrolase including carboxyl esterase, lipase, pectin esterase, and chlorophlyllase. Especially effective among them is lipase.

Trade names of commercial products and producers are as follows: "Alkalase", "Esperase", "Savinase", "AMG", "BAN", "Fungamill", "Sweetzyme", "Thermamyl" (Novo Industry, Copenhagen, Denmark); "Maksatase", "High-alkaline protease", "Amylase THC", "Lipase" (Gist Brocades, N.V., Delft, Holland); "Protease B-400", "Protease B-4000", "Protease AP", "Protease AP 2100" (Schweizerische Ferment A.G., Basel, Switzerland); "CRD Protease" (Monsanto Company, St. Louis, Mo.); "Piocase" (Piopin Corporation, Monticello, Ill.); "Pronase P", "Pronase AS", "Pronase AF" (Kaken Chemical Co., Ltd., Japan); "Lapidase P-2000" (Lapidas, Secran, France); protease products (Tyler standard sieve, 100% pass 16 mesh and 100% on 150 mesh) (Clington Corn Products, Division of Standard Brands Corp., New York); "Takamine", "Bromelain 1:10", "HT Protease 200", "Enzyme L-W" (obtained from fungi, not from bacteria) (Miles Chemical Company, Elkhart, Ind.); "Rhozyme P-11 Conc.", "Pectinol", "Lipase B", "Rhozyme PF", "Rhozyme J-25" (Rohm & Haas, Genencor, South San Francisco, Calif.); "Ambrozyme 200" (Jack Wolf & Co., Ltd., Subsidiary of Nopco Chemical Company, Newark, N.J.); "ATP 40", "ATP 120", "ATP 160" (Lapidas, Secran, France); "Oripase" (Nagase & Co., Ltd., Japan).

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified one. This enzyme should be used in the form of granules made of crude enzyme alone or in combination with other components in the detergent composition. Granules of crude enzyme are used in such an amount that the purified enzyme its 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic surfactants and long-chain fatty acid salts

Such cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference The composition may contain from about 1 to about 20 weight percent of such cationic surfactants and long-chain fatty acid salts.

Builders

A. Divalent sequestering agents.

The composition may contain from about 0 to about 50 weight percent of one or more builder components selected. from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering agents are disclosed in British Patent Application No. 2 094 82-6 A, the disclosure of which is incorporated herein by reference.

B. Alkalis or inorganic electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethylcellulose or/and polyethylene glycol with the cellulase composition of the present invention provides for an especially useful dirt removing composition.

Bleaching agents

The use of the cellulase of the present invention in combination with a bleaching agent such as sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the deterging effects.

Bluing agents and fluorescent dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, clay, calcium silicate (such as Micro-Cell of Johns Manville Co.), calcium carbonate and magnesium oxide.

Masking agents for factors inhibiting the cellulase activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as the inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-activators

The activators vary depending on variety of the cellulases. In the presence of proteins, cobalt and its salts, magnesium and its salts, and calcium and its salts, potassium and its salts, sodium and its salts or mono-saccharides such as mannose and xylose, the cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzenesulfonate salts such as p-toluenesulfonate salts, glycols such as propylene glycol, acetylbenzenesulfonate salts, acetamides, pyridinedicarboxylic acid amides, benzoate salts and urea.

The detergent composition of the present invention can be used in a broad pH range of from acidic to alkaline pH. In a preferred embodiment, the detergent composition of the present invention can be used in alkaline detergent wash media and more preferably, alkaline detergent wash media having a pH of from above 7 to no more than about 8.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. The granules have a size of from 50 to 2000 micrometers. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention are used in industrial and household uses at temperatures and liquor ratios conventionally employed in these environments.

In addition to their use in laundry detergents, the cellulase compositions described herein can additionally be used in a pre-washing step in the appropriate solution at an intermediate pH where sufficient activity exists to provide desired improvements in color retention/restoration, softening and feel. When the cellulase composition is employed in a pre-soak (e.g., pre-wash) composition, either as a liquid, spray, gel or paste composition, the cellulase composition is generally employed from about 0.01 to about 20 weight percent based on the total weight of the pre-soak composition. In such compositions, a surfactant may optionally be employed and when employed, is generally present at a concentration of from about 0.01 to about 20 weight percent based on the total weight of the pre-soak. The remainder of the composition comprises conventional components used in the pre-soak, i.e., diluent, buffers, other enzymes (proteases), and the like at their conventional concentrations. Accordingly, such pre-soak compositions comprise from about 0 to about 20 weight percent of a surfactant and from about 0.01 to about 20 weight percent of a cellulase comprising one or more EG type components and less than about 5 weight percent CBH I type components.

Also, it is contemplated that the cellulase compositions described herein can also be used in home use as a stand alone composition suitable for restoring color to faded fabrics. See, for example, U.S. Pat. No. 4,738,682, which is incorporated herein by reference in its entirety.

The following examples are offered to illustrate the present invention and should not be construed in any way as limiting the scope of this invention.

EXAMPLES

Examples 1–12 demonstrate the preparation of *Trichoderma longibrachiatum* genetically engineered so as to be incapable of producing one or more cellulase components or so as to overproduce specific cellulase components.

Example 1

Selection for pyr4⁻ mutants of *Trichoderma longibrachiatum*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of *Trichoderma longibrachiatum* strain RL-P37 (Sheir-Neiss G. and Montenecourt, B. S., 1984, Appl. Microbiol. Biotechnol. 20:46–53) were spread on the surface of a solidified medium containing 2 mg/ml uridine and 1.2 mg/ml FOA. Spontaneous FOA-resistant colonies appeared within three to four days and it was possible to subsequently identify those FOA-resistant mutants which required uridine for growth. In order to identify those mutants which specifically had a defective pyr4 gene, protoplasts were generated and transformed with a plasmid containing a wild-type pyr4 gene (see Examples 3 and 4). Following transformation, protoplasts were plated on medium lacking uridine. Subsequent growth of transformed colonies demonstrated complementation of a defective pyr4 gene by the plasmid-borne pyr4 gene. In this way strain GC69 was identified as a pyr4-mutant of strain RL-P37.

Example 2

Preparation of CBHI Deletion Vector

A cbh1 gene encoding the CBHI protein was cloned from the genomic DNA of strain RL-P37 by hybridization with an oligonucleotide probe designed on the basis of the published sequence for this gene using known probe synthesis methods (Shoemaker et al., "Molecular Cloning of Exo-cellobiohydrolase I Derived from *Trichoderma longibrachiatum* Strain L27", *Bio/Technology* 1, p. 691 (1983). The cbh1 gene resides on a 6.5 kb PstI fragment and was inserted into PstI cut pUC4K (purchased from Pharmacia Inc., Piscataway, N.J.) replacing the Kan$^r$ gene of this vector. The resulting plasmid, pUC4K::cbhI was then cut with HindIII and the larger fragment of about 6 kb was isolated and religated to give pUC4K::cbhIΔH/H. This procedure removes the entire cbh1 coding sequence and approximately 1.2 kb upstream and 1.5 kb downstream of flanking DNA from either side of the original PstI fragment.

The *Trichoderma longibrachiatum* pyr4 gene was cloned as a 6.5 kb fragment of genomic DNA in pUC18 following the methods of Sam brook et al., 1989, Molecular Cloning, A Laboratory Manual, 2$^{nd}$ ED., Cold Springs Harbor Press. The plasmid pUC4K::cbhIΔH/H was cut with HindIII and the ends were desphosphorylated with calf intestinal alkaline phosphatase. This end dephosphorylated DNA was ligated with the 6.5 kb HindIII fragment containing the *Trichoderma longibrachiatum* pyr4 gene to give pΔCBHIpyr4. See FIG. 1.

Example 3

Isolation of Protoplasts

Mycelium was obtained by inoculating 100 ml of YEG (0.5% yeast extract, 2% glucose) in a 500 ml flask with about 5×10⁷ *Trichoderma longibrachiatum* GC69 spores (the pyr4⁻ mutant strain). The flask was then incubated at 37° C. with shaking for about 16 hours. The mycelium was harvested by centrifugation at 2,750×g. The harvested mycelium was further washed in 1.2 M sorbitol solution and resuspended in 40 ml of Novozym$^R$ 234 solution (which is the tradename for a multicomponent enzyme system containing 1,3-alpha-glucanase, 1,3-beta-glucanase, laminarinase, xylanase, chitinase and protease from Novo Biolabs, Danbury Conn.) containing 5 mg/ml Novozym$^R$ 234; 5 mg/ml MgSO$_4$.7H$_2$O; 0.5 mg/ml bovine serum albumin; 1.2 M sorbitol. The protoplasts were removed from cellular debris by filtration through Miracloth (Calbiochem. Corp, LaJolla, Calif.) and collected by centrifugation at 2,000×g. The protoplasts were washed three times in 1.2 M sorbitol and once in 1.2 M sorbitol, 50 MM CaCl$_2$, centrifuged and resuspended. The protoplasts were finally resuspended at a density of 2×10⁸ protoplasts per ml of 1.2 M sorbitol, 50 mM CaCl$_2$.

Example 4

Transformation of Fungal Protoplasts

200 μl of the protoplast suspension prepared in Example 3 was added to 20 μl of EcoRI digested pΔCBHIpyr4 (prepared in Example 2) in TE buffer (10 mM Tris, pH 7.4; 1 mM EDTA) and 50 μl of a polyethylene glycol (PEG) solution containing 25% PEG 4000, 0.6 M KCl and 50 mM CaCl$_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2 M sorbitol and 50 mM CaCl$_2$ was added thereto and this solution was further mixed. The protoplast solution was then immediately added to molten aliquots of Vogel's Medium N (3 grams sodium citrate, 5 grams KH$_2$PO$_4$, 2 grams NH4NO$_3$, 0.2 grams MgSO$_4$.7H$_2$O, 0.1 gram CaCl$_2$.2H$_2$O, 5 μg α-biotin, 5 mg citric acid, 5 mg ZnSO$_4$.7H$_2$O, 1 mg Fe(NH$_4$)$_2$.6H$_2$O, 0.25 mg CuSO$_4$.5H$_2$O, 50 μg MnSO4.4H$_2$O per liter) containing an additional 1% glucose, 1.2 M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene present in pΔCBHIpyr4. These colonies were subsequently transferred and stable transformants purified, on a solid Vogel's medium N containing as an additive, 1% glucose.

Example 5

Analysis of the Transformants

DNA was isolated from the transformants obtained in Example 4 after they were grown in the liquid Vogel's medium N containing 1% glucose. These transformant DNA samples were further cut with a PstI restriction enzyme subjected to agarose gel electrophoresis. The gel was further blotted onto a Nytran membrane filter and hybridized with a $^{32}$P labelled pΔCBHIpyr4 probe. The probe was selected to identify the native cbh1 gene as a 6.5 kb PtI fragment, the native pyr4 gene and any DNA sequences derived from the transforming DNA fragment. FIG. 2 outlines deletion of the *Trichoderma longibrachiatum* cbh1 gene by integration of the larger EcoR1 fragment from pΔCBHIpyr4 at the cbh1 locus on one of the *Trichoderma longibrachiatum* chromosomes.

The bands from the hybridization were visualized via autoradiography. The result of the autoradiograph is seen in FIG. 3. Five samples were run as described above, hence samples A, B, C, D, and E. Lane E is the untransformed strain GC69 and was used as a control in the present analysis. Lanes A–D represent transformants obtained from the methods described above. The numbers on the side of the autoradiograph represent the sizes of molecular weight markers. As can be seen from this autoradiograph, Lane D does not contain the 6.5 kb CBHI band, indicating that this gene has been totally deleted in the transformant. This cbh1 deleted strain is called P37PΔCBHI. The other transformants analyzed appear identical to the untransformed control strain. Presumably, this happened. because the linear fragment from pΔCBHIpyr4 integrated by a double crossover at the native Pyr4 locus to give a gene replacement event.

Example 6

The same procedure was used in this example as in Example 5, except that the probe used was changed to a $^{32}P$ labelled pIntCBHI probe. This probe is a pUC-type plasmid containing a 2 kb BglII fragment from the cbh1 locus within the region that was deleted in pUC4::cbh1ΔH/H. Two samples were run in this example including a control sample A, which is the untransformed strain GC69 and the transformant P37PΔCBHI, sample B. As can be seen in FIG. 4, sample A contained the cbh1 gene, as indicated by the band at 6.5 kb; however the transformant, sample B does not contain this 6.5 kb band and therefore does not contain the cbh1 gene.

Example 7

Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO$, 0.03% $MgSO_4$, 0.03% urea, 0.75% bactotryptone, 0.05% Tween 80, 0.000016% $CuSO_4 \cdot 5H_2O$, 0.001% $FeSO_4 \cdot 7H_2O$, 0.000128% $ZnSO_4 \cdot 7H_2O$, 0.0000054% $Na_2MoO_4 \cdot 2H_2O$, 0.0000007% $MnCl4H_2O$). The medium was incubated while shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. while shaking. The supernatant was then collected from these cultures and the mycelium was discarded. Samples of the culture supernatant were analyzed by isoelectric focusing using a Pharmacia Phastgel system and pH 3–9 precast gels according to the manufacturer's instructions. The gel was stained with silver stain to visualize the protein bands. The band corresponding to the cbh1 protein was absent from the sample derived from the strain P37PΔCBHI, as shown in FIG. 5. This isoelectric focusing gel shows various proteins in different supernatant cultures of Trichoderma longibrachiatum. Lane A is partially purified CBH I; Lane B is the supernatant from an untransformed Trichoderma longibrachiatum culture; Lane C is the supernatant from a strain deleted for the cbh1 gene produced according to the methods of the present invention. The position of various cellulase components are labelled. Since CBH I constitutes about 50% of the total extracellular protein, it is the major secreted protein and hence is the darkest band on the gel. This isoelectric focusing gel clearly shows depletion of the CBH I protein in the strain. deleted for cbh1.

Example 8

Preparation of pPΔCBHII

The cbh2 gene of Trichoderma longibrachiatum, encoding the CBH II protein, has been cloned as a 4.1 kb EcoRI fragment of genomic DNA which is shown diagramatically in FIG. 6A (Chen et al., 1987, Biotechnology, 5:274–278). Using methods known in the art, a plasmid, pPΔCBHII (FIG. 6B), has been constructed in which a 1.7 kb central region of this clone between a HindIII site (at 74 bp 3' of the CBHII translation initiation site) and a ClaI site (at 265 bp 3' of the last codon of CBHII) has been removed and replaced by the Trichoderma longibrachiatum pyr4 gene.

Digestion of this plasmid with EcoRI will liberate a fragment having 0.7 kb of flanking DNA from the cbh2 locus at one end, 1.7 kb of flanking DNA from the cbh2 locus at the other end and the Trichoderma longibrachiatum pyr4 gene in the middle.

Example 9

Generation of a pyr4⁻ mutant of P37PΔCBHI

Spores of the transformant (P37PΔCBHI) which was deleted for the cbh1 gene were spread onto medium containing FOA. A pyr4⁻ derivative of this transformant was subsequently obtained using the methods of Example 1. This pyr4⁻ strain was designated P37PΔCBHIPyr⁻26.

Example 10

Deletion of cbh2 Gene in a Strain Previously Deleted for cbh1

Protoplasts of strain P37PΔCBHIPyr⁻26 were generated and transformed with EcoRI digested pPΔCBHII according to the methods outlined in Examples 3 and 4.

Purified stable transformants were cultured in shake flasks as in Example 7 and the protein in the culture supernatants was examined by isoelectric focusing. One transformant (designated P37PΔCBH67) was identified which did not produce any CBH II protein. Lane D of FIG. 5 shows the supernatant from a strain deleted for both the cbh1 and cbh2 genes produced according to the methods of the present invention.

DNA was extracted from strain P37PΔCBH67, digested with EcoRI and Asp718, and subjected to agarose gel electrophoresis. The DNA from this gel was blotted to a membrane filter and hybridized with $^{32}p$ labelled pPΔCBHII (FIG. 7). Lane A of FIG. 7 shows the hybridization pattern observed for DNA from an untransformed Trichoderma longibrachiatum strain. The 4.1 kb EcoRI fragment containing the wild-type cbh2 gene was observed. Lane B shows the hybridization pattern observed for strain P37PΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern analysis was performed as above. In this example, the probe was $^{32}P$ labelled pIntCBHII. This plasmid contains a portion of the cbh2 gene coding sequence from within that segment of cbh2 DNA which was deleted in plasmid pPΔCBHII. No hybridization was seen with DNA from strain P37PΔCBH67 showing that the cbh2 gene was deleted and that no sequences derived from the pUC plasmid were present in this strain.

Example 11

Construction of pEGIpyr4

The *Trichoderma longibrachiatum* egl1 gene, which encodes EGI, has been cloned as a 4.2 kb HindIII fragment of genomic DNA from strain RL-P37 by hybridization with oligonucleotide(s synthesized according to the published sequence (Penttila et al., 1986, Gene 45:253–263). A 3.6 kb HindIII-BamHI fragment was taken from this clone and ligated with a 1.6 kb HindIII-BamHI fragment containing the *Trichoderma longibrachiatum* pyr4 gene and a pUC-based plasmid cut with HindIII to give the plasmid pEGIpyr4 (FIG. 8). Digestion of pEGIpyr4 with HindIII would liberate a fragment of DNA containing only *Trichoderma longibrachiatum* genomic DNA (the egl1 and pyr4 genes) except for 24 bp of sequenced, synthetic DNA between the two genes and 6 bp of sequenced, synthetic DNA at one end (see FIG. 8).

Example 12

Transformants of *Trichoderma longibrachiatum* Containing pEGIpyr4

A pyr4 defective mutant of *Trichoderma longibrachiatum* strain RutC30 (Sheir-Neiss and Montenecourt, 1984, Appl. Microbiol. Biotechnol. 20:46–53) was obtained by the method outlined in Example 1. Protoplasts of this strain were transformed with undigested pEGIpyr4 and stable transformants were purified. Five of these transformants (designated EP2, EP4, EP5, EP6, EP11), as well as untransformed RutC30 were inoculated into 50 ml of YEG medium (yeast extract, 5 g/l; glucose, 20 g/l) in 250 ml shake flasks and cultured with shaking for 2 days at 28$° C. The resulting mycelium was washed with sterile water and added to 50 ml of TSF medium (0.05M citrate-phosphate buffer, pH 5.0; Avicel microcrystalline cellulose, 10 g/l; $KH_2PO_4$, 2.0 g/l; $(NH_4)_2SO_4$, 1.4 g/l; proteose peptone, 1.0 g/l; Urea, 0.3 g/l; $MgSo_4.7H_2O$, 0.3 g/l; $CaCl_2$, 0.3 g/l; $FeSO_4.7H_2O$, 5.0 mg/l; $MnSO_4.H_2O$, 1.6 mg/l; $ZnSO_4$, 1.4 mg/l; $CoCl_2$, 2.0 mg/l; 0.1% Tween 80). These cultures were incubated with shaking for a further 4 days at 28° C. Samples of the supernatant were taken from these cultures and assays designed to measure the total amount of protein and of endoglucanase activity were performed as described below.

The endoglucanase assay relied on the release of soluble, dyed oligosaccharides from Remazol Brilliant Blue—carboxymethylcellulose (RBB-CMC, obtained from MegaZyme, North Rocks, NSW, Australia). The substrate was prepared by adding 2 g of dry RBB-CMC to 80 ml of just boiled deionized water with vigorous stirring. When cooled to room temperature, 5 ml of 2 M sodium acetate buffer (pH 4.8) was added and the pH adjusted to 4.5. The volume was finally adjusted to 100 ml with deionized water and sodium azide added to a final concentration of 0.02%. Aliquots of Trichoderma reesei culture supernatant or 0.1 M sodium acetate as a blank (10–20 μl) were placed in tubes, 250 μl of substrate was added and the tubes were incubated for 30 minutes at 37° C. The tubes were placed on ice for 10 minutes and 1 ml of cold precipitant (3.3% sodium acetate, 0.4% zinc acetate, pH 5 with HCl, 76% ethanol) was then added. The tubes were vortexed and allowed to sit for 5 minutes before centrifuging for 3 minutes at approximately 13,000×g. The optical density was measured spectrophotometrically at a wavelength of 590–600 nm.

The protein assay used was the BCA (bicinchoninic acid) assay using reagents obtained from Pierce, Rockford, Ill., USA. The standard was bovine serum albumin (BSA). BCA reagent was made by mixing 1 part of reagent B with 50 parts of reagent A. One ml of the BCA reagent was mixed with 50 μl of appropriately diluted BSA or *Trichoderma longibrachiatum* culture supernatant. Incubation was for 30 minutes; at 37° C. and the optical density was finally measured spectrophotometrically at a wavelength of 562 nm.

The results of the assays described above are shown, in Table 1. It is clear that some of the transformants produced increased amounts of endoglucanase activity compared to untransformed strain RutC30. It is thought that the endoglucanases or exo-cellobiohydrolases produced by untransformed *Trichoderma longibrachiatum* constitute approximately 20% and 70% respectively of the total amount of protein secreted. Therefore a transformant such as EP5, which produces approximately four-fold more endoglucanase than strain RutC30, would be expected to secrete approximately equal amounts of endoglucanase-type and exo-cellobiohydrolase-type proteins.

The transformants described in this example were obtained using intact pEGIpyr4 and will contain DNA sequences integrated in the genome which were derived from the pUC plasmid. Prior to transformation it would be possible to digest pEGIpyr4 with HindIII and isolate the larger DNA fragment containing only *Trichoderma longibrachiatum* DNA. Transformation of *Trichoderma longibrachiatum* with this isolated fragment of DNA would allow isolation of transformants which overproduced EGI and contained no heterologous DNA sequences except for the two short pieces of synthetic DNA shown in FIG. 8. It would also be possible to use pEGIpyr4 to transform a strain which was deleted for either the cbh1 gene, or the cbh2 gene, or for both genes. In this way a strain could be constructed which would over-produce EGI and produce either a limited range of, or no, exo-cellobiohydrolases.

The methods of Example 12 could be used to produce *Trichoderma longibrachiatum* strains which would overproduce any of the other endoglucanases normally produced by *Trichoderma longibrachiatum* (*T. reesei*).

| STRAIN | A<br>ENDOGLUCANASE<br>ACTIVITY<br>(O.D. AT 590 nm) | B<br>PROTEIN<br>(mg/ml) | A/B |
| --- | --- | --- | --- |
| RutC30 | 0.32 | 4.1 | 0.078 |
| EP2 | 0.70 | 3.7 | 0.189 |
| EP4 | 0.76 | 3.65 | 0.208 |
| EP5 | 1.24 | 4.1 | 0.302 |
| EP6 | 0.52 | 2.93 | 0.177 |
| EP11 | 0.99 | 4.11 | 0.241 |

The above results are presented for the purpose of demonstrating the overproduction of the EGI component and not for the purpose of the extent of overproduction. In this regard, the extent of overproduction is expected to vary with each experiment.

Example 13 demonstrates the isolation of the components of CYTOLASE 123 Cellulase (a complete fungal cellulase composition obtained from *Trichoderma longibrachiatum* and available from Genencor International, Inc., South San Francisco, Calif.) via purification procedures.

Example 13

Purification of Cytolase 123 Cellulase into Cellulase Components

CYTOLASE 123 cellulase was fractionated in the following manner. The normal distribution of cellulase components in this cellulase system is as follows:

| | |
|---|---|
| CBH I | 45–55 weight percent |
| CBH II | 13–15 weight percent |
| EG I | 11–13 weight percent |
| EG II | 8–10 weight percent |
| EG III | 1–4 weight percent |
| BG | 0.5–1 weight percent. |

The fractionation was done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin. The fraction bound on this column contained CBH I and EG I. These components were separated by gradient elution using an aqueous gradient containing from 0 to about 500 mM sodium chloride. The fraction not bound on this column contained CBH II and EG II. These fractions were desalted using a column of Sephadex G-25 gel filtration resin equilibrated with 10 mM sodium citrate, pH 3.3. This solution, 200 ml, was then loaded onto a column of 20 ml of SP Trisacryl M cation exchange resin. CBH II and EG II were eluted separately using an aqueous gradient containing from 0 to about 200 mM sodium chloride.

Following procedures similar to that of Example 13 above, other cellulase systems which can be separated into their components include CELLUCAST (available from Novo Industry, Copenhagen, Denmark), RAPIDASE (available from Gist Brocades, N.V., Delft, Holland), and cellulase systems derived from *Trichoderma koningii*, Penicillum sp. and the like.

Example 14

Purification of EG III from CYTOLASE 123 Cellulase

Example 13 above demonstrated the isolation of several components from Cytolase 123 Cellulase. However, because EG III is present in very small quantities in Cytolase 123 Cellulase, the following procedures were employed to isolate this component.

A. Large Scale Extraction of EG III Cellulase Enzyme

One hundred liters of cell free cellulase filtrate were heated to about 30° C. The heated material was made about 4% wt/vol PEG 8000 (polyethylene glycol, MW of about 8000) and about 10% wt/vol anhydrous sodium sulfate. The mixture formed a two phase liquid mixture. The phases were separated using an SA-1 disk stack centrifuge. The phases were analyzed using silver staining isoelectric focusing gels. Fractionation and enrichment were obtained for EG III and xylanase. The recovered composition contained about 20 to 50 weight percent of EG III.

Regarding the above procedure, use of a polyethylene glycol having a molecular weight substantially less than about 8000 gave inadequate separation; whereas, use of polyethylene glycol having a molecular weight substantially greater than about 8000 resulted in the exclusion of desired enzymes in the recovered composition. With regard to the amount of sodium sulfate, sodium sulfate levels substantially greater than about 10% wt/vol caused precipitation problems; whereas, sodium sulfate levels substantially less than about 10%wt/vol gave poor separation or the solution remained in a single phase.

B. Purification of EG III Via Fractionation

The purification of EG III is conducted by fractionation from a complete fungal cellulase composition (CYTOLASE 123 cellulase, commercially available from Genencor International, South San Francisco, Calif.) which is produced by wild type *Trichoderma longibrachiatum*. Specifically, the fractionation is done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, is desalted using a column of 3 liters of Sephadex G-25 gel filtration resin with 10 mM sodium phosphate buffer at pH 6.8. The desalted solution, is then loaded onto a column of 20 ml of QA Trisacryl M anion exchange resin. The fraction bound on this column contains CBH I and EG I. The fraction not bound on this column contains CBH II, EG II and EG III. These fractions are desalted using a column of Sephadex G-25 gel filtration resin equilibrated with 10 mM sodium citrate, pH 4.5. This solution, 200 ml, is then loaded onto a column of 20 ml of SP Trisacryl M cation exchange resin. The EG III was eluted with 100 mL of an aqueous solution of 200 mM sodium chloride.

In order to enhance the efficiency of the isolation of EG III, it may be desirable to employ *Trichoderma reesei* genetically modified so as to overexpress EG III and/or to be incapable of producing one or more of EG I, EG II, CBH I and/or CBH II components. This will necessarily lead to the more efficient isolation of EG III by, for example, fractionation and/or PEG extraction as described above.

Likewise, it may be desirable for the EG III compositions described above to be further purified to provide for substantially pure EG III compositions, i.e., compositions containing EG III at greater than about 80 weight percent of protein. For example, such a substantially pure EG III protein can be obtained by utilizing material obtained from procedure A in procedure B or vice versa. One particular method for further purifying EG III is by further fractionation of an EG III sample obtained in part b) of this Example 14. The further fraction was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in part b) of this Example 14 with a 20 ml Sephadex G-25 column which had been previously equilibrated with 10 mM sodium citrate pH 4. The column was then eluted with 0–200 mM aqueous gradient of NaCl at a rate of 0.5 ml/minute with samples collected in 1 ml fractions. EG III was recovered in fractions 10 and 11 and was determined to be greater than 90% pure by SDS gel electrophoresis. EG III of this purity is suitable for determining the N-terminal amino acid sequence by known techniques.

Substantially pure EG III as well as EG I and EG II components purified in Example 13 above can be used singularly or in mixtures in the methods of this invention. These EG components have the following characteristics:

|        | MW         | pI  | pH optimum[1] |
|--------|------------|-----|---------------|
| EG I   | ~47–49 kD  | 4.7 | ~5            |
| EG II  | ~35 kD     | 5.5 | ~5            |
| EG III | ~25–28 kD  | 7.4 | ~5.5–6.0      |

[1]. pH optimum determined by RBB-CMC activity as per Example 15 below.

The use of a mixture of these components in the practice of this invention may give a synergistic response in improving softening, color retention/restoration and/or feel as compared to a single component. On the other hand, the use of a single component in the practice of this invention may be more stable or have a broader spectrum of activity over a range of pHs. For instance, Example 15 below shows that EG III has considerable activity against RBB-CMC under alkaline conditions.

Example 15

Activity of Cellulase Compositions Over a pH Range

The following procedure was employed to determine the pH profiles of two different cellulase compositions. The first cellulase composition was a CBH I and II deleted cellulase composition prepared from *Trichoderma longibrachiatum* genetically modified in a manner similar to that described above so as to be unable to produce CBH I and CBH II components. Insofar as this cellulase composition does riot contain CBH I and CBH II which generally comprise from about 58 to 70 percent of a cellulase composition derived from *Trichoderma longibrachiatum*, this cellulase composition is necessarily enriched in EG components, i.e., EG I, EG II,, EG III and the like.

The second cellulose composition was an approximately 20–40% pure fraction of EG III isolated from a cellulase composition derived from Trichoderma reesei via purification methods similar to part b) of Example 14.

The activity of these cellulase compositions was determined at 40° C. and the determinations were made using the following procedures.

Add 5 to 20 μl of an appropriate enzyme solution at a concentration sufficient to provide the requisite amount of enzyme in the final solution. Add 250 pl of 2 weight percent RBB-CMC (Remazol Brilliant Blue R-Carboxymethylcellulose—commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 μl of methyl cellosolve containing 0.3M sodium acetate and 0.02M zinc acetate. Vortex and let sit for 5–10 minutes. Centrifuge and pour supernatant into cuvets. Relative enzyme activity was determined by measuring the optical density (OD) of the solution in each cuvet at 590 nm. Higher levels of optical density correspond to higher levels of enzyme activity.

The results of this analysis are set forth in FIG. 9 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. On the other hand, the cellulase composition enriched in EG III possesses optimum cellulolytic activity at about pH 5.5–6 and possesses significant activity at alkaline pHs.

Example 16

Launderometer Strength Loss Assay Cellulase Compositions

The purpose of this example is to examine the ability of different cellulase compositions to reduce the strength of cotton-containing fabrics. Because the activity of most of the cellulase components derived from *Trichoderma longibrachiatum* is greatest at or near pH 5, strength loss results will be most evident when the assay is conducted at about this pH. However, the results achieved at pH 5 are believed to correlate with strength loss results which would occur at other pHs and accordingly, are indicative of the relative strength loss capacity of the cellulase components analyzed.

Specifically, in this example, the first cellulase composition analyzed was a complete fungal cellulase composition (CYTOLASE 123 cellulase, commercially available from Genencor International, South San Francisco, Calif.) produced by wild type Trichoderma reesei and is identified as GC010.

The second cellulase composition analyzed was a CBH II deleted cellulase composition prepared from *Trichoderma longibrachiatum* genetically modified in a manner similar to Examples 1 to 12 above so as to be incapable of expressing CBH II and is identified as CBHIId. Insofar as CBH II comprises up to about 15 percent of the cellulase composition, deletion of this component results in enriched levels of CBH I, and all of the EG components.

The third cellulase composition analyzed was a CBH I and CBH II deleted cellulase composition prepared from *Trichoderma longibrachiatum* genetically modified in a manner similar to that described above so as to be incapable of expressing CBH I and CBH II and is identified as CBHI/IId. Insofar as CBH I and CBH II comprises up to about 70 percent of the cellulase composition, deletion of this component results in enriched levels of all of the EG components.

The last cellulase composition analyzed was a CBH I deleted cellulase composition prepared from *Trichoderma longibrachiatum* genetically modified in a manner similar to that described above so as to be incapable of expressing CBH I and is identified as CBHId. Insofar as CBH I comprises up to about 55 percent of the cellulase composition, deletion of this component results in enriched levels of CBH II and all of the EG components.

The cellulase compositions described above were tested for their effect on cotton-containing fabric strength loss in a launderometer. The compositions were first normalized so that equal amounts of EG components were used. Each cellulase composition was then added to separate solutions of 400 ml of a 20 mM citrate/phosphate buffer, titrated to pH 5, and which contains 0.5 ml of a non-ionic surfactant. Each of the resulting solutions was then added to a separate launderometer canister. Into these canisters were added a quantity of marbles to facilitate strength loss as well as a 16 inch×20 inch cotton fabric (100% woven cotton, available as Style No. 467 from Test Fabrics, In(c., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

In order to maximize strength loss results, the above procedure was repeated twice more and after the third treatment, the cotton fabrics were removed and analyzed for strength loss. Strength loss was measured by determining the tensile strength in the fill direction ("FTS") using a Instron Tester and the results compared to the FTS of the fabric treated in the same solution with the exception that no cellulase was added. The results of this analysis are reported as % strength loss which is determined as follows:

$$\% \text{ Strength Loss} = 100 \times \left[ 1 - \frac{FTS \text{ with cellulase}}{FTS \text{ without cellulase}} \right]$$

The results of this analysis are set forth in FIG. 10 which shows that compositions containing CBH I, i.e., whole cellulase (GC010) and CBH II deleted cellulose, possessed the most strength loss whereas, the compositions containing no CBH I possessed significantly reduced strength loss as compared to whole cellulase and CBH II deleted cellulase. From these results, it is seen that the presence of CBH I in a cellulase composition imparts increased strength loss to the composition as compared to a similar composition not containing CBH I.

Likewise, these results show that CBH II plays some role in strength loss. Accordingly, in view of these results, when strength loss resistant cellulase compositions are desired, such compositions should be free of all CBH I type cellulase components and preferably, all CBH type cellulase components. In this regard, it is contemplated that EG enriched cellulase compositions will result in even lower strength loss at pH >7 than those results observed at pH 5 shown in FIG. 10.

Example 17

Color Restoration

The ability of EG enriched cellulase to restore color in cotton-containing fabrics was analyzed in the following experiments. Specifically, color restoration of a worn cotton fabric arises from the accumulation on the fabric of surface fibers over a period of time. These fibers give rise to a faded and matted appearance for the fabric and accordingly, the removal of these fibers is a necessary prerequisite to restoring the original sharp color to the fabric. In view of the above, these experiments determine the ability of a cellulase composition to restore color by measuring the ability of the cellulase composition to remove surface fibers.

The first experiment measures the ability of a complete cellulase system (CYTOLASE 123 cellulose, commercially available from Genencor International, South San Francisco, Calif.) produced by wild type *Trichoderma longibrachiatum* to remove surface fibers from a cotton-containing fabric over various pHs. This cellulase was tested for its ability to remove surface fibers in a launderometer. An appropriate amount of cellulase to provide for either 25 ppm or 100 ppm cellulase in the final composition was added to separate solutions of 400 ml of a 20 mM citrate/phosphate buffer containing 0.5 ml of a non-ionic surfactant. Samples were prepared and titrated so as to provide for samples at pH 5, pH 6, pH 7 and pH 7.5. Each of the resulting solutions was then added to a separate launderometer canister. Into these canisters were added a quantity of marbles to facilitate fiber removal as well as a 7 inch×5 inch cotton fabric (100% woven cotton, available as Style No. 439W from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

The so treated fabrics were then analyzed for fiber removal by evaluation in a panel test. In particular, the coded fabrics (i.e., unmarked) were rated for levels of fiber by 6 individuals. The fabrics were visually evaluated for surface fibers and rated on a 0 to 6 scale. The scale has six standards to allow meaningful comparisons. The standards are as follows:

| Rating | Standard[2] |
|---|---|
| 0 | Fabric not treated with cellulase |
| 1 | Fabric treated[3] with 8 ppm cellulase |
| 2 | Fabric treated with 16 ppm cellulase |
| 3 | Fabric treated with 20 ppm cellulase |
| 4 | Fabric treated with 40 ppm cellulase |
| 5 | Fabric treated with 50 ppm cellulase |
| 6 | Fabric treated with 100 ppm cellulase |

[2]In all of the standards, the fabric was a 100% cotton sheeting standardized test fabric (Style No. 439W) available from Test Fabrics, Inc., 200 Blackford Ave., Middlesex, NJ 08846
[3]For all samples treated with the same cellulase composition. Cellulase concentrations are in total protein. The launderometer treatment conditions are the same as set forth in Example 16 above.

The fabric to be rated was provided a rating which most closely matched one of the standards. After complete analysis of the fabrics, the values assigned to each fabric by all of the individuals were added and an average value generated.

The results of this analysis are set forth in FIG. 11. Specifically, FIG. 11 illustrates that at the same pH, a dose dependent response is seen in the amount of fibers removed. That is to say that at the same pH, the fabrics treated with more cellulase provided for higher levels of fiber removal as compared to fabrics treated with less cellulase. Moreover the results of this figure demonstrate that at higher pHs, fiber removal can still be effected merely by using higher concentrations of cellulase.

In a second experiment, two different cellulase compositions were compared for the ability to remove fiber. Specifically, the first cellulase composition analyzed was a complete cellulase system (CYTOLASE 123 cellulase, commercially available from Genencor International, South San Francisco, Calif.) produced by wild type *Trichoderma longibrachiatum* and is identified as GC010.

The second cellulase composition-analyzed was a CBH I and CBH II deleted cellulase composition prepared from *Trichoderma longibrachiatum* genetically modified in a manner similar to that described above so as to be incapable of producing CBH I and CBH II and is identified as CBHI/IId. Insofar as CBH I and CBH II comprises up to about 70 percent of the cellulase composition, deletion of this component results in enriched levels of all of the EG components.

The cellulase compositions were first normalized so that similar amounts of EG components were used. These compositions were tested for their ability to remove surface fibers in a launderometer. An appropriate amount of cellulase to provide for the requisite concentrations of EG components in the final compositions were added to separate solutions of 400 ml of a 20 mM citrate/phosphate buffer containing 0.5 ml of a non-ionic surfactant. Samples were prepared and titrated to pH 5. Each of the resulting solutions was then added to a separate launderometer canister. Into these canisters were added a quantity of marbles to facilitate fiber removal as well as a 7 inch×5 inch cotton fabric (100% woven cotton, available as Style No. 439W from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

The so treated fabrics were then analyzed for fiber removal by evaluation in the panel test described above. The results of this analysis are set forth in FIG. 12. Specifically, FIG. 12 illustrates that both GC010 and CBH I/IId cellulase compositions gave substantially identical fiber removal results when equal amounts of EG are used. These results suggest that it is the EG components which provide for fiber removal. These results coupled with the results of FIG. 11 demonstrate that EG components can remove fibers even under alkaline conditions.

Example 18

Tergotometer Color Restoration

This example is further to Example 17 and substantiates that CBH type components are not necessary for color restoration. The purpose of this example is to examine the ability of cellulase compositions deficient in CBH type components to restore color to cotton-containing fabrics. Because the activity of most of the EG components derived from *Trichoderma longibrachiatum* is greatest at or near pH 5, color restoration results will be most evident when the assay is conducted at about this pH. However, the results achieved at pH 5 are believed to correlate with color restoration results which would occur at other pHs and accordingly, are indicative of the relative color restoration capacity of the cellulase components analyzed.

Specifically, the cellulase composition employed in this example was a CBH I and CBH II deleted cellulase composition prepared from *Trichoderma longibrachiatum* genetically modified in a manner similar to that described above so as to be incapable of producing CBH I and CBH II. Insofar as CBH I and CBH II comprises up to about 70 percent of the cellulase composition, deletion of this component results in enriched levels of all of the-EG components.

The assay was conducted by adding a sufficient concentration of this cellulase composition to a 50 mM citrate/phosphate buffer to provide 500 ppm of cellulase. The solution was titrated to pH 5 and contained 0.1 weight percent of nonionic surfactant (Grescoterg GL100—commercially available from Gresco Mfg., Thomasville, N.C. 27360). A 10 inch×10 inch faded cotton-containing fabric was then placed into 1 liter of this buffer and allowed to sit at 110° F. for 30 minutes and then agitated for 30 minutes at 100 rotations per minute. The fabrics were then removed from the buffer, washed and dried. The resulting fabrics were then compared to the fabric prior to treatment. The results of this analysis are as follows:

| Cotton-Containing Material | Result |
| --- | --- |
| Worn Cotton T-Shirt | benefit seen |
| Cotton Knit | benefit seen |

The term "benefit seen" means that the treated fabric exhibits color restoration (i.e., is less faded) as compared to the non-treated fabric. These results substantiate the results of Example 17 that the presence of CBH type components is not necessary for effecting color restoration of faded cotton-containing fabrics.

Example 19

Softness This example demonstrates that the presence of CBH type components are not essential for imparting improved softness to cotton-containing fabrics. Specifically, this example employs a cellulase composition derived from *Trichoderma longibrachiatum* genetically engineered in the manner described above so as to be incapable of producing CBH I and II components.

This cellulase composition was tested for its ability to soften terry wash cloth. Specifically, unsoftened 8.5 ounce cotton terry cloths, 14 inches by 15 inches (available as Style No. 420NS from Test Fabrics, Inc., 200 Blackford Ave., Middlesex, N.J. 08846), were cut into 7 inch by 7.5 inch swatches.

The cellulase composition described above was tested for its ability to soften these swatches in a launderometer. Specifically, an appropriate amount of cellulase to provide for 500 ppm, 250 ppm, 100 ppm, 50 ppm, and 10 ppm cellulase in the final cellulase solution was added to separate solutions of 400 ml of a 20 mM citrate/phosphate buffer containing 0.025 weight percent of a non-ionic surfactant (Triton X114). Additionally, a blank was run containing the same solution but with no added cellulase. Samples so prepared were titrated to pH 5. Each of the resulting solutions was then added to a separate launderometer canister. Into these canisters were added a quantity of marbles to facilitate softness as well as cotton swatches described above. All conditions were run in triplicate with two swatches per canister. Each canister was then closed and the canister lowered into the launderometer bath which was maintained at 37° C. The canister was then rotated in the bath at a speed of at least about 40 revolutions per minute (rpms) for about 1 hour. Afterwards, the swatches were removed, rinsed well and dried in a standard drier.

The swatches were then analyzed for softness by evaluation in a preference test. Specifically, six panelists were given their own set of swatches and ask to rate them with respect to softness based on softness criteria such as the pliability of the whole fabric. Swatches obtained from treatment with the five different enzyme concentrations and the blank were placed behind a screen and the panelists were asked to order them from least soft to most soft. Scores were assigned to each swatch based on its order relative to the other swatches; 5 being most soft and 0 being least soft. The scores from each panelists were cumulated and then averaged.

The results of this averaging are set forth in FIG. 13. Specifically, these results demonstrate that at higher cellulase concentrations, improved softening is obtained. It is noted that this improved softening is achieved without the presence of either CBH I or II in the cellulase composition.

With regard to these results, it is contemplated that with lower concentrations of the cellulase composition, improved softening will manifest itself over repeated washings.

With regard to Examples 16 to 19, cellulase compositions enriched in EG type components derived front microorganisms other than *Trichoderma longibrachiatum* could be used in place of the cellulase compositions described in these examples. In particular, the source of the cellulase composition enriched in EG type components is not important to this invention and any fungal cellulase composition enriched in EG type components can be used. For example, fungal cellulases for use in preparing the fungal cellulase compositions used in this invention can be obtained from *Trichoderma koningii*, Pencillum sp., and the like or commercially available cellulases can be used, i.e., CELLUCLAST (available from Novo Industry, Copenhagen, Denmark), RAPIDASE (available from Gist Brocades, N.V., Delft, Holland), and the like.

What is claimed is:

1. A detergent composition comprising:
   (a) a cleaning effective amount of a surfactant or a mixture of surfactants; and
   (b) a fungal cellulase composition in a sufficient amount to impart color restoration/retention and softness to a cotton garment wherein said cellulase composition comprises one or more endoglucanase components and less than about 5 weight percent of exo-cellobiohydrolase components based on the weight of protein in the cellulase composition.

2. A detergent composition according to claim 1 wherein said cellulase composition comprises from about 0.05 to about 2 weight percent of said detergent composition.

3. A detergent composition according to claim 1 wherein said cellulase composition is free of all exo-cellobiohydrolase components.

4. A detergent composition according to claim 3 wherein said cellulase composition is derived from a genetically modified microorganism incapable of expressing any exo-cellobiohydrolase components and/or capable of overexpressing one or more endoglucanase components.

5. A detergent composition according to claim 1 wherein said cellulase composition is derived from a genetically modified microorganism incapable of expressing any exo-cellobiohydrolase components.

6. A detergent composition according to claim 5 wherein said cellulase composition does not contain any heterologous proteins.

7. A method for enhancing the softness of a cotton-containing fabric which method comprises washing the fabric in a wash medium derived from a detergent composition comprising (a) from about 5 weight percent to about 95 weight percent of a surfactant or a mixture of surfactants; and (b) a fungal cellulase composition in a sufficient amount to impart color restoration/retention and softness to a cotton garment wherein said cellulase composition comprises one or more endoglucanase components and less than about 5 weight percent of exo-cellobiohydrolase components based on the weight of protein in the cellulase composition.

8. A method according to claim 7 wherein said cellulase composition comprises from about 0.05 to about 2 weight percent of said detergent composition.

9. A method according to claim 7 wherein said cellulase composition is free of all exo-cellobiohydrolase components.

10. A method according to claim 7 wherein said cellulase composition is derived from a genetically modified microorganism incapable of producing any exo-cellobiohydrolase components and/or capable of overexpressing one or more endoglucanase components.

11. A method according to claim 7 wherein said cellulase composition is derived from a genetically modified microorganism incapable of expressing any exo-cellobiohydrolase components.

12. A method according to claim 11 wherein said cellulase composition does not contain any heterologous proteins.

13. A method for retaining/restoring the color of a cotton-containing fabric which method comprises washing the fabric one or more times in a wash medium derived from a detergent composition comprising (a) from about 5 weight percent to about 95 weight percent of a surfactant or a mixture of surfactants; and (b) of a fungal cellulase composition in a sufficient amount to impart color restoration/retention and softness to a cotton garment wherein said cellulase composition comprises one or more endoglucanase components and less than about 5 weight percent of exo-cellobiohydrolase components based on the weight of protein in the cellulase composition.

14. A method according to claim 13 wherein said cellulase composition comprises from about 0.05 to about 2 weight percent of said detergent composition.

15. A method according to claim 13 wherein said cellulase composition is free of all exo-cellobiohydrolase components.

16. A method according to claim 13 wherein said cellulase composition is derived from a genetically modified microorganism incapable of producing any exo-cellobiohydrolase components and/or capable of overexpressing one or more endoglucanase components.

17. A method according to claim 13 wherein said cellulase composition is derived from a genetically modified microorganism incapable of expressing any exo-cellobiohydrolase components.

18. A method according to claim 17 wherein said cellulase composition does not contain any heterologous proteins.

* * * * *

Adverse Decision in Interference

Patent No. 6,162,782, Kathleen A. Clarkson, Edward Larenas, Sharon Shoemaker, Geoffrey L. Weiss, DETERGENT COMPOSITIONS CONTAINING CELLULASE COMPOSITIONS DEFICIENT IN CBH I TYPE COMPONENTS, Interference No. 105,155, final judgment adverse to the patentees rendered April 26, 2006, as to claims 1-18.

(*Official Gazette February 13, 2007*)